(12) United States Patent
Urban et al.

(10) Patent No.: US 10,030,260 B2
(45) Date of Patent: Jul. 24, 2018

(54) INDUCIBLE RECONSTITUTION AND REAL-TIME QUANTITATIVE KINETIC SYSTEM FOR THE STUDY OF INTRAMEMBRANE ENZYMES

(71) Applicant: THE JOHNS HOPKINS UNIVERSITY, Baltimore, MD (US)

(72) Inventors: Sinisa Urban, Baltimore, MD (US); Rosanna Baker, Baltimore, MD (US); Seth Dickey, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 205 days.

(21) Appl. No.: 14/436,139

(22) PCT Filed: Oct. 16, 2013

(86) PCT No.: PCT/US2013/065186
§ 371 (c)(1),
(2) Date: Apr. 16, 2015

(87) PCT Pub. No.: WO2014/062771
PCT Pub. Date: Apr. 24, 2014

(65) Prior Publication Data
US 2015/0267243 A1    Sep. 24, 2015

Related U.S. Application Data

(60) Provisional application No. 61/714,417, filed on Oct. 16, 2012.

(51) Int. Cl.
*C12Q 1/37* (2006.01)
*G01N 33/573* (2006.01)

(52) U.S. Cl.
CPC ............ *C12Q 1/37* (2013.01); *G01N 33/573* (2013.01); *G01N 2333/952* (2013.01); *G01N 2500/04* (2013.01)

(58) Field of Classification Search
None
See application file for complete search history.

(56) References Cited

U.S. PATENT DOCUMENTS

| 7,718,391 B2 | 5/2010 | Freeman |
| 2010/0285988 A1 | 11/2010 | Shelton et al. |

FOREIGN PATENT DOCUMENTS

WO    03-008635 A2    1/2003

OTHER PUBLICATIONS

Nestorovich et al., "Residue Ionization and Ion Transport through OmpF Channels", Biophysical Journal, 2003, vol. 85, pp. 3718-3729.*
Urban, et al., "Reconstitution of intramembrane proteolysis in vitro reveals that pure rhomboid is sufficient for catalysis and specificity", PNAS, Feb. 8, 2005, vol. 102, No. 6, pp. 1883-1888.
Baker, et al., "Enzymatic analysis of a rhomboid intramembrane protease implicates transmembrane helix 5 as the lateral substrate gate", PNAS, May 15, 2007, vol. 104, No. 20, pp. 8257-8262.
Baker, et al. "Architectural and thermodynamic principles underlying intramembrane protease function", Nature Chemical Biology, Sep. 2012, vol. 8, pp. 759-768.
Bondar, et al., "Rhomboid protease dynamics and lipid interactions", Structure, Mar. 11, 2009, vol. 17, pp. 395-405.
Chavez-Gutierrez, et al., "The mechanism of y-secretase dysfunction in familial alzheimer disease", The EMBO Journal, (2012), vol. 31, No. 10, pp. 2261-2274.
Lemberg, et al., "Mechanism of intramembrane proteolysis investigated with purified rhomboid proteases", The EMBO Journal, (2005), vol. 24, No. 3, pp. 464-472.
Lemberg, et al., "Functional and evolutionary implications of enhanced genomic analysis of rhomboid intramembrane proteases", Genome Research, (2007), vol. 17, pp. 1634-1646.
Moin, et al., "Membrane immersion allows rhomboid proteases to achieve specificity by reading transmembrane segment dynamics", eLIFE, (2012), vol. 1:e00173.
Pierrat, et al., "Monocyclic B-lactams are selective, mechanism-based inhibitors of rhomboid intramembrane proteases", American Chemical Society, (2011), vol. 6, pp. 325-335.
Amarneh, et al., "Rhomboid proteases: familiar features in unfamiliar phases", Molecular Cell, Dec. 24, 2009, vol. 36, pp. 922-923.
Strisovsky, et al., "Sequence-specific intramembrane proteolysis: identification of a recognition motif in rhomboid substrates", Molecular Cell, Dec. 24, 2009, vol. 36, pp. 1048-1059.
Adrian, et al. (2012) "New lives for old: evolution of pseudoenzyme function illustrated by iRhoms" Nature reviews Molecular cell biology 13, 489-498.
Brunger, et al. (1998) "Crystallography & NMR System: A New Software Suite for Macromolecular Structure Determination" Acta Cryst, D54, 905-921.

(Continued)

*Primary Examiner* — Suzanne M Noakes
(74) *Attorney, Agent, or Firm* — Johns Hopkins Technology Ventures

(57) ABSTRACT

The present invention relates to the field of enzymes. More specifically, the present invention provides an inducible reconstitution and real-time quantitative kinetic system for the study of intramembrane enzymes. In a specific embodiment, a method of screening for modulators of an intramembrane protease comprises the steps of (a) contacting in a mixture the protease and a substrate with a lipid under acidic or basic conditions to form a membrane comprising the lipid bilayer, protease and the substrate; (b) contacting a test agent with the membrane mixture; (c) adjusting the pH to physiological conditions; (d) assaying substrate cleavage by the protease; and (e) comparing the assayed substrate cleavage to a reference that does not include the test agent, wherein an increase or a decrease of substrate cleavage by the protease relative to the reference identifies the test agent as a modulator of the intramembrane protease.

18 Claims, 24 Drawing Sheets

(56) References Cited

OTHER PUBLICATIONS

Casci, et al. (1999) "Control of EGF receptor signalling: Lessons from fruitflies" Cancer and Metastasis Reviews 18: 181-201.
Bailey, Collaborative Computational Project (1994) "The CCP4 suite: programs for protein crystallography" Acta Cryst, D50, 760-763.
Datsenko, et al. (2000) "One-step inactivation of chromosomal genes in *Escherichia coli* K-12 using PCR products" PNAS, vol. 97, No. 12, pp. 6640-6645.
Strooper, et al. (2010) "Novel Research Horizons for Presenilins and γ-Secretases in Cell Biology and Disease" Annu. Rev. Cell Dev. Biol. 26:235-60.
Deckert, et al. (1998) "The complete genome of the hyperthermophilic bacterium Aquifex aeolicus" Nature, vol. 293.
Doucet, et al. (2008) "Metadegradomics; Toward in vivo quantitative degradomics of proteolytic post-translational modifications of the cancer proteome", Molecular & Cellular Proteomics 7:1925-1951.
Drag, et al. (2010) "Emerging principles in protease-based drug discovery" Nature Reviews, vol. 9, pp. 690-701.
Elrod, et al. (1980) "Protonic reorganization and substrate structure in catalysis by serine proteases" Journal of the American Chemical Society, vol. 102, No. 11.
Emsley, et al. (2004) "Coot: model-building tools for molecular graphics" Acta Cryst. D60, 2126-2132.
Fleig, et al. (2012) "Ubiquitin-Dependent Intramembrane Rhomboid Protease Promotes ERAD of Membrane Proteins", Molecular Cell 47, 558-569.
Fluhrer, et al. (2009) "Intramembrane Proteolysis by Signal Peptide Peptidases: A Comparative Discussion of GXGD-type Aspartyl Proteases" The Journal of Biological Chemistry vol. 284, No. 21, pp. 13975-13979.
Friedman, et al. (2010) "Detection of Damaged DNA Bases by DNA Glycosylase Enzymes", Biochemistry 49, 4957-4967.
Gallio, et al. (2002) "A conserved mechanism for extracellular signaling in eukaryotes and prokaryotes", PNAS, vol. 99, No. 19, pp. 12208-12213.
Hummell, et al. (1962) "Measurement of protein-binding phenomena by gel filtration" Biochim. Biophys. Acta, 63, pp. 530-532.
Huntington (2012) "Thrombin plasticity" Biochimica et Biophysica Acta 1824 pp. 246-252.
Kuznetsov, et al. (2007) "Kinetic Conformational Analysis of Human 8-Oxoguanine-DNA Glycosylase" The Journal of Biological Chemistry vol. 282, No. 2, pp. 1029-1038.
Lazareno-Saez, et al. (2013) "Domain Swapping in the Cytoplasmic Domain of the *Escherichia coli* Rhomboid Protease" J. Mol. Biol. 425, pp. 1127-1142.
Li, et al.(2009) "Cleavage of RseA by RseP requires a carboxyl-terminal hydrophobic amino acid following DegS cleavage" PNAS, vol. 106, No. 35, pp. 14837-14842.
Li, et al. (2013) "Structure of a presenilin family intramembrane aspartate protease", Nature, vol. 493.
Lopez-Otin, et al. (2008) "Proteases: Multifunctional Enzymes in Life and Disease", The Journal of Biological Chemistry vol. 283, No. 45, pp. 30433-30437.
Makinoshima, et al. (2006) "Site-2 proteases in prokaryotes: regulated intramembrane proteolysis expands to microbial pathogenesis" Microbes and Infection 8 1882-1888.
Murshudov, et al. (2011) "REFMAC5 for the refinement of macromolecular crystal structures", Acta Crystallographica D67, pp. 355-367.

Osenkowski, et al. (2008) "Direct and Potent Regulation of γ-Secretase by Its Lipid Microenvironment", The Journal of Biological Chemistry vol. 283, No. 33, pp. 22529-22540.
Otwinowski, et al. (1997) "Processing of x-ray diffraction data collected in oscillation mode" Methods in Enzymology, vol. 276, No. 21, pp. 307-326.
Perona, et al. (1997) "Evolutionary Divergence of Substrate Specificity within the Chymotrypsin-like Serine Protease Fold", The Journal of Biological Chemistry, vol. 272, No. 48, pp. 29987-29990.
Zhou, et al.(2012) "An Internal Water-Retention Site in the Rhomboid Intramembrane Protease GlpG Ensures Catalytic Efficiency", Structure 20, 1255-1263.
Rather, et al. (1999) "Providencia stuartii Genes Activated by Cell-to-Cell Signaling and Identification of a Gene Required for Production or Activity of an Extracellular Factor", Journal of Bacteriology, vol. 181, No. 23, pp. 7185-7191.
Schnaitman (1970) "Protein Composition of the Cell Wall and Cytoplasmic Membrane of *Escherichia coli*" Journal of Bacteriology, vol. 104, No. 2, pp. 890-901.
Schnaitman (1970) "Examination of the Protein Composition of the Cell Envelope of *Escherichia coli* by Polyacrylamide Gel Electrophoresis" Journal of Bacteriology, vol. 104, No. 2, pp. 882-889.
Shah, et al. (2005) "Nicastrin Functions as a γ-Secretase-Substrate Receptor", Cell, vol. 122, pp. 435-447.
Stennick, et al. (2000) "Internally quenched fluorescent peptide substrates disclose the subsite preferences of human caspases 1, 3, 6, 7 and 8", Biochem. J. 350, 563-568.
Stevenson, et al. (2007) "Rhomboid protease AarA mediates quorum-sensing in Providencia stuartii by activating TatA of the twin-arginine translocase", PNAS, vol. 104, No. 3, pp. 1003-1008.
Timmer, et al. (2009) "Structural and kinetic determinants of protease substrates", Nature Structural & Molecular Biology, vol. 16 No. 10.
Zhang, et al.(2006) "Deuterium Solvent Isotope Effect and Proton-Inventory Studies of Factor Xa-Catalyzed Reactions", Biochemistry 45, 14175-14182.
Urban, et al. (2008) "In vivo analysis reveals substrate-gating mutants of a rhomboid intramembrane protease display increased activity in living cells", Biol Chem. 389(8): 1107-1115.
Urban (2009) "Making the cut: central roles of intramembrane proteolysis in pathogenic microorganisms", Nature Reviews Microbiology, vol. 7.
Urban, et al.(2011) "The rhomboid protease family: a decade of progress on function and mechanism", Genome Biology, 12:231.
Vinothkumar, et al. (2010) "The structural basis for catalysis and substrate specificity of a rhomboid protease", The EMBO Journal 29, 3797-3809.
Wilderman, et al. (2002) "Pseudomonas aeruginosa Synthesizes Phosphatidylcholine by Use of the Phosphatidylcholine Synthase Pathway", Journal of Bacteriology, vol. 184, No. 17, pp. 4792-4799.
Wolfe (2009) "Intramembrane proteolysis", Chem Rev., vol. 109, No. 4, pp. 1599-1612.
Wu, et al. (2006) "Structural analysis of a rhomboid family intramembrane protease reveals a gating mechanism for substrate entry", Nature Structural & Molecular Biology vol. 13 No. 12.
Xue, et al. (2012) "Catalytic Mechanism of Rhomboid Protease GlpG Probed by 3,4-Dichloroisocoumarin and Diisopropyl Fluorophosphonate", The Journal of Biological Chemistry vol. 287, No. 5, pp. 3099-3107.
Xue, et al. (2012) "Conformational Change in Rhomboid Protease GlpG Induced by Inhibitor Binding to Its S' Subsites", Biochemistry 51, 3723-3731.

* cited by examiner

A

B

C

A

B

INDUCIBLE RECONSTITUTION AND REAL-TIME QUANTITATIVE KINETIC SYSTEM FOR THE STUDY OF INTRAMEMBRANE ENZYMES

CROSS-REFERENCE TO RELATED APPLICATIONS

This application is a 35 U.S.C. § 371 U.S. national entry of International Application PCT/US2013/065186, having an international filing date of Oct. 16, 2013, which claims the benefit of U.S. Provisional Application No. 61/714,417, filed Oct. 16, 2012, the content of each of the aforementioned applications is herein incorporated by reference in their entirety.

STATEMENT OF GOVERNMENTAL INTEREST

This invention was made with government support under grant no. 2R01AI066025-07A1, awarded by the National Institutes of Health. The government has certain rights in the invention.

FIELD OF THE INVENTION

The present invention relates to the field of enzymes. More specifically, the present invention provides an inducible reconstitution and real-time quantitative kinetic system for the study of intramembrane enzymes.

INCORPORATION-BY-REFERENCE OF MATERIAL SUBMITTED ELECTRONICALLY

This application contains a sequence listing. It has been submitted electronically via EFS-Web as an ASCII text file entitled "P12181-02_Sequence_Listing_ST25.txt." The sequence listing is 1,507 bytes in size, and was created on Oct. 16, 2013. It is hereby incorporated by reference in its entirety.

BACKGROUND OF THE INVENTION

Each protein in a living cell will be cleaved by a protease (Doucet et al., 2008; Lopez-Otin and Bond, 2008). The purpose of these enzymatic events ranges from shredding damaged proteins that might otherwise harm the cell, to sculpting signal precursors to initiate cell communication (Lopez-Otin and Bond, 2008). Aside from controlling essential processes in all forms of life, protease inhibition has proven to be a particularly effective therapeutic strategy, especially in hypertension and antiviral treatment (Drag and Salvesen, 2010).

Ultimately deciphering how a protease shapes the signaling characteristics of healthy cells, or targeting it for therapeutic intervention in disease, requires a sophisticated understanding of its enzymatic properties. Kinetic dissection of protease catalysis has been key in revealing these properties (Huntington, 2012; Perona and Craik, 1997; Timmer et al., 2009). Coupled with structural analyses, these studies have established that both cytosolic and extracellular proteases are designed to bind their substrates specifically at discrete sites, with affinity reflected in the Michaelis constant ($K_M$), and endowed with catalytic residues that function in rate enhancement, reflected in the turnover number ($k_{cat}$). The catalytic efficiency of a protease is the quotient of these two parameters, and typically ranges from $10^4$-$10^7 M^{-1}s^{-1}$ ($10^8$ reflects enzymes whose activity is limited by diffusion).

Intramembrane proteases, in contrast to these well-studied soluble proteases, are a more recently-discovered class of extraordinary enzymes that evolved independently to catalyze hydrolysis immersed within the membrane (De Strooper and Annaert, 2010; Fluhrer et al., 2009; Makinoshima and Glickman, 2006; Urban and Dickey, 2011; Wolfe, 2009). Despite this complexity, there is significant incentive for understanding how proteolysis is accomplished within these constraints, because intramembrane proteases hold great promise for developing therapies: rhomboid proteases are implicated in Parkinson's disease and parasite invasion (Urban and Dickey, 2011); γ-secretase in Alzheimer's disease and leukemia (De Strooper and Annaert, 2010; Wolfe, 2009); signal peptide peptidases in immunity and hepatitis C virus assembly (Fluhrer et al., 2009); and site-2 proteases in the virulence of some of the world's deadliest bacterial and fungal pathogens (Makinoshima and Glickman, 2006; Urban, 2009).

Major insights into the molecular architecture of these remarkable enzymes has been gained from a series of high-resolution intramembrane protease crystal structures of prokaryotic orthologs (Li et al., 2013; Wolfe, 2009), as led by analyses of the *Escherichia coli* rhomboid protease GlpG (as summarized in (Urban, 2010). In contrast, analysis of catalysis within the membrane in quantitative terms has not been achieved with any intramembrane protease, making it difficult to decipher their functional properties. Current models are based largely on extrapolations from soluble proteases, which evolved independently and could be different. In fact, the membrane is a fundamentally unusual setting for proteolysis: chemically, the membrane is viscous and excludes water, which is both essential for proteolysis and affects how proteins interact. Spatially, proteins in a membrane exist in a two-dimensional plane and are orientationally-confined relative to each other. Although techniques for studying proteins inside the membrane are scarce, understanding the consequences of this environment, and how intramembrane proteases function within it, requires interrogating the kinetics of proteolysis within its natural membrane setting.

We have overcome multiple inherent limitations to develop the first 'inducible' membrane reconstitution system for the quantitative analysis of rhomboid proteolysis occurring within the membrane and in real time. The results reveal that, contrary to expectations, rhomboid proteolysis is a slow reaction that is not driven by affinity of enzyme for substrate. Instead, these insights suggest a completely different mode of action for this ancient and widespread family of enzymes.

SUMMARY OF THE INVENTION

The present invention is based, at least in part, on the development of an inducible reconstitution system for studying intramembrane enzymes. Many enzymes implicated in diseases such as Alzheimer's disease, Parkinson's disease, and malaria and tuberculosis infection, function within cell membranes. However, no assay has ever been developed that can monitor catalysis actually occurring within its natural membrane setting in real-time and quantitatively. The present inventors have developed such an assay, which will be useful for a broad range of enzymes and for their detailed study as well as drug screening and evaluation.

The key problem with previous assays has been that the process of putting both enzyme and substrate into the membrane results in premature catalysis before scientists can study them. The present inventors developed conditions that allow the enzyme to stay off, and then turn it on for the analysis of catalysis. There are several options that work for essentially all enzymes. Moreover, with regard to real-time analysis, it has been very difficult to make a fluorogenic substrate that works in membranes. The present inventors discovered that, in certain embodiments, putting a fluorophore at a particular position of the substrate results in natural quenching in membranes. The enzyme once turned on releases it by catalysis, resulting in a very sensitive, quantitative and reproducible assay in real-time that works in multi-channel plates (miniaturized and high throughput).

In certain embodiments, reconstituting the protease and substrate in a lipid membrane under acidic conditions eliminates premature cleavage. In a specific embodiment, the acidic conditions comprise about pH 4. In a more specific embodiment, the membrane is reconstituted at pH 4.0. Without being bound by a particular theory, in certain embodiments, the low pH protonates the catalytic histidine, rendering it catalytically-inactive. In other embodiments, reconstituting the protease and substrate under basic conditions eliminates premature cleavage. Then, in some embodiments, after collecting the proteoliposomes by ultracentrifugation, the reaction can be initiated by adjusting the pH to physiological conditions. In a specific embodiment, physiological conditions comprise about pH 7.4. In a more specific embodiment, the reaction is initiated at pH 7.4. Any intramembrane protease can be used in the system of the present invention. In certain embodiments, the protease is a rhomboid protease. In other embodiments, γ-secretases or signal peptide peptidases are used. In other embodiments, site-2 protease are reconstituted in membranes and studied. Any intramembrane protease that uses catalytic histidines can be used in the present invention. Additional protease that can be used include the ZAMP 1 Ste24 CAAX protease, a Zn-dependent metalloprotease with a ring of 8 transmembrane segments. Another CAAX processing family member includes Rec1 (Ras-converting enzyme 1), a true intramembrane protease having catalytic glutamate and histidine residues. In general, any intramembrane protease that is pH sensitive can be used as described herein.

In particular embodiments, the substrate is a natural substrate for the particular protease used. In specific embodiments, the substrate is a protein or peptide. In certain embodiments, the substrate is conjugated with a detectable label. In some embodiments, the detectable label is conjugated to the amino-terminus of the substrate. In other embodiments, the detectable label is conjugated to the carboxy-terminus of the substrate. The label could also be conjugated as a side chain at any internal position of the substrate. In more particular embodiments, the label is conjugated to an extracellular or intracellular portion of the substrate.

DETAILED DESCRIPTION OF THE INVENTION

Figures 1A, 1B:
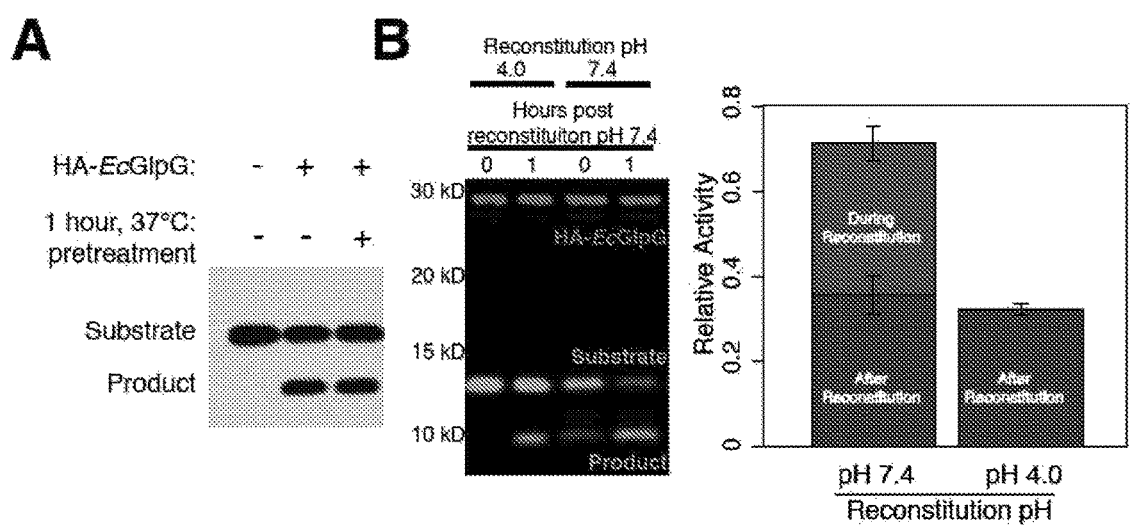
FIG. 1. An inducible co-reconstitution system for membrane enzyme analysis. (A) HA-tagged GlpG (HA-EcGlpG) preincubated for 1 hour at 37° C. retained full activity against the substrate APP+Spi7-Flag (shown is an anti-Flag western). (B) HA-EcGlpG was inactive during the reconstitution with APP+Spi7-Flag at pH 4, but active when reconstituted at pH 7.4 (t=0 reaction times). Activity was restored upon neutralization to pH 7.4 (see 1 h reaction time). Shown is a 2-color western, and quantification (graph) revealing the amount of protease activity in proteoliposomes was indistinguishable whether the protease was subjected to pH shift or not. (C) Thermostability of HA-EcGlpG without and after pretreatment in pH 4 buffer was examined by heating from 25 to 85° C. and monitoring differential static light scattering every 0.5° C. (D) X-ray crystal structure comparison of ΔN-EcGlpG at low (red) and neutral (blue) pH. Note that although the overall conformation is indistinguishable (Cα RMSD=0.32 Å), at low pH the catalytic serine 201 sidechain was no longer hydrogen-bonded to the histidine base (inset), rendering the enzyme catalytically inactive. See Table 51 for structural parameters.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "modulate" indicates the ability to control or influence directly or indirectly, and by way of non-limiting examples, can alternatively mean inhibit or stimulate, agonize or antagonize, hinder or promote, alter and strengthen or weaken. Furthermore, by "modulation" or "modulates" is meant a change (increase or decrease) in the expression level or biological activity of a gene or polypeptide as detected by standard methods known in the art. As used herein, modulation includes at least about 10% change, 25%, 40%, 50% or a greater change in expression levels or biological activity (e.g., about 75%, 85%, 95% or more). A "modulator" is an agent that modulates. Thus, the term "intramembrane protease modulator" refers to an agent that modulates an intramembrane protease.

Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease associated with the modulated intramembrane protease.

As used herein, an "antagonist" is a type of modulator and the term refers to an agent that binds a target (e.g., a protein) and can inhibit a one or more functions of the target. For example, an antagonist of a protein can bind the protein and inhibit the binding of a natural or cognate ligand to the protein and/or inhibit signal transduction mediated through the protein. The term can be used interchangeably with the term "inhibitor."

An "agonist" is a type of modulator and refers to an agent that binds a target and can activate one or more functions of the target. For example, an agonist of a protein can bind the protein and activate the protein in the absence of its natural or cognate ligand.

An "agent" is a compound, polynucleotide, or polypeptide that modulates the biological activity of a target gene or polypeptide. A "test agent" is an agent to be tested for its modulatory activity on an intramembrane protease.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

An "amino acid analog" refers to a compound that has the same basic chemical structure as a naturally occurring amino acid, i.e., a carbon that is bound to a hydrogen, a carboxyl group, an amino group, and an R group (e.g., homoserine, norleucine, methionine sulfoxide, methionine methyl sulfonium), but that contains some alteration not found in a naturally occurring amino acid (e.g., a modified side chain). The term "amino acid mimetic" refers to chemical compounds that have a structure that is different from the general chemical structure of an amino acid, but that function in a manner similar to a naturally occurring amino acid. Amino acid analogs may have modified R groups (for example, norleucine) or modified peptide backbones, but retain the same basic chemical structure as a naturally occurring amino acid. In one embodiment, an amino acid analog is a D-amino acid, a beta-amino acid, or an N-methyl amino acid.

Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

By "antibody" is meant any immunoglobulin polypeptide, or fragment thereof, having immunogen binding ability.

By "fragment" is meant a portion (e.g., at least about 5, 10, 25, 50, 100, 125, 150, 200, 250, 300, 350, 400, or 500 amino acids or nucleic acids) of a protein or nucleic acid molecule that is substantially identical to a reference protein or nucleic acid and retains at least one biological activity of the reference. In some embodiments the portion retains at least 50%, 75%, or 80%, or more preferably 90%, 95%, or even 99% of the biological activity of the reference protein or nucleic acid described herein.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

The term "nucleic acid" refers to an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

Specific examples of some nucleic acids envisioned for this invention may contain phosphorothioates, phosphotriesters, methyl phosphonates, short chain alkyl or cycloalkyl intersugar linkages or short chain heteroatomic or heterocyclic intersugar linkages. Also preferred are oligonucleotides having morpholino backbone structures (Summerton, J. E. and Weller, D. D., U.S. Pat. No. 5,034,506). In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone (P. E. Nielsen et al. Science 199: 254, 1997). Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form. Some specific examples of such modified bases include 2-(amino)adenine, 2-(methylamino)adenine, 2-(imidazolylalkyl)adenine, 2-(aminoalklyamino)adenine, or other heterosubstituted alkyladenines.

The term "protein" refers to proteins, polypeptide and/or peptides.

The term "reference" means a standard or control condition.

By "subject" or "patient" is meant a mammal, including, but not limited to, a human or non-human mammal, such as a bovine, equine, canine, ovine, or feline.

II. Screening Assays

As reported herein, the activity of an intramembrane protease (e.g., a rhomboid protease, a γ-secretase, a presenilin, a signal peptide peptidase or a site-2 protease) can be studied using the inducible reconstitution system of the present invention. Accordingly, compounds or agents that modulate the expression or activity of an intramembrane protease are useful in the methods of the present invention for the treatment or prevention of a disease or disorder associated with the protease.

In a specific embodiment, a method of screening for modulators of an intramembrane protease comprises the steps of (a) contacting in a mixture the protease and a substrate with a lipid under acidic or basic conditions to form a membrane comprising the lipid bilayer, protease and the substrate; (b) contacting a test agent with the membrane mixture; (c) adjusting the pH to physiological conditions; (d) assaying substrate cleavage by the protease; and (e) comparing the assayed substrate cleavage to a reference that does not include the test agent, wherein an increase or a decrease of substrate cleavage by the protease relative to the reference identifies the test agent as a modulator of the intramembrane protease. In particular embodiments, the method further comprises collecting the membrane by, for example, ultracentrifugation, biobead incubation or gel filtration chromatography. In one embodiment, the intramembrane protease is a rhomboid protease. In another embodiment, the intramembrane protease is a γ-secretase. In a further embodiment, the intramembrane protease is a signal peptide peptidase. In yet another embodiment, the intramembrane protease is a site-2 protease. In further embodiments, the intramembrane protease is a presenilin homolog, prepilin peptidase, preflagellin peptidase or a signal peptide peptidase. In certain embodiments, the substrate is a protein. In other embodiments, the protein being studied is an intramembrane enzyme. In particular embodiments, the intramembrane protein is a kinase.

In certain embodiments, the acidic conditions comprise about pH 3 to about pH 5. In a more specific embodiment, the acidic conditions comprise about pH 4. In a more specific embodiment, the acidic conditions comprise pH 4. In particular embodiments, the physiological conditions comprise about pH 7.4. In a specific embodiment, physiological conditions comprise pH 7.4. In other embodiments, physiological conditions comprise pH 5 to about pH 9. Physiological conditions can comprise about pH 7 to about pH 9, pH 7 to about pH 9, pH 7 to about pH 8, pH 7 to pH 8, and the like. In other embodiments, the substrate comprises a detectable label. In more specific embodiments, the detectable label is conjugated to the amino terminus of the substrate. In other embodiments, the detectable label is conjugated to the carboxy terminus of the substrate. In further embodiments, the detectable label is conjugated to the extracellular or intracellular domain of the substrate. In particular embodiments, the placement of the label depends on the cleavage site of the substrate by the protease. For example, certain γ-secretases release the c-terminal part of the substrate protein into the cytoplasm. In such cases, the label can be placed at the c-terminal part of the substrate.

The present invention also provides methods of screening for modulators of an intramembrane rhomboid protease comprising the steps of (a) contacting in a mixture the protease and a substrate with a lipid at pH 4.0 to form a membrane comprising the lipid bilayer, protease and the substrate; (b) contacting a test agent with the membrane mixture; (c) raising the pH to pH 7.4; (d) assaying substrate cleavage by the protease; and (e) comparing the assayed substrate cleavage to a reference that does not include the test agent, wherein an increase or a decrease of substrate cleavage by the protease relative to the reference identifies the test agent as a modulator of the intramembrane protease.

In another embodiment, a method for identifying inhibitors of an intramembrane rhomboid protease comprises the steps of (a) contacting in a mixture the protease and a substrate with a lipid at pH 4.0 to form a membrane comprising the lipid bilayer, protease and the substrate; (b) contacting a test agent with the membrane mixture; (c) raising the pH to pH 7.4; (d) assaying substrate cleavage by the protease; and (e) comparing the assayed substrate cleavage to a reference that does not include the test agent, wherein a decrease of substrate cleavage by the protease relative to the reference identifies the test agent as an inhibitor of the intramembrane rhomboid protease.

In yet another embodiment, a method for identifying agonists of an intramembrane rhomboid protease comprises the steps of (a) contacting the protease and a substrate with a lipid at pH 4.0 to form a membrane comprising the lipid bilayer, protease and the substrate; (b) contacting a test agent with the membrane mixture; (c) raising the pH to pH 7.4; (d) assaying substrate cleavage by the protease; and (e) comparing the assayed substrate cleavage to a reference that does not include the test agent, wherein an increase of substrate cleavage by the protease relative to the reference identifies the test agent as an agonist of the intramembrane rhomboid protease.

In some embodiments, it may be desirable to incubate the test agents with the membrane mixture (e.g., substrate/protease liposome mixture) for a period of time prior to initiating the reaction. In one embodiment, this could be implemented by delivering the rhomboid-containing liposomes at pH 4, pre-incubating for a set time, followed by activating rhomboid proteolysis by injecting neutralizing buffer. The rhomboid protease is already stable at pH 4 in a 384-well plate for at least 1 hour at 37° C., and upon addition of neutralization solution regains full activity. In some embodiments, libraries of test agents/compounds that are pH-stable can be used. In other embodiments, the enzyme could be maintained at pH 4 during the reconstitution step, but then neutralize to a slightly higher pH (4.5 to 5.5) for preincubation with the compounds. This intermediate pH could maintain the enzyme off sufficiently to ensure low assay background yet be gentle enough to preserve/limit any potential adverse effects on the compounds themselves. The reactions would then be initiated by neutralizing to pH 7.4.

Figure 12:
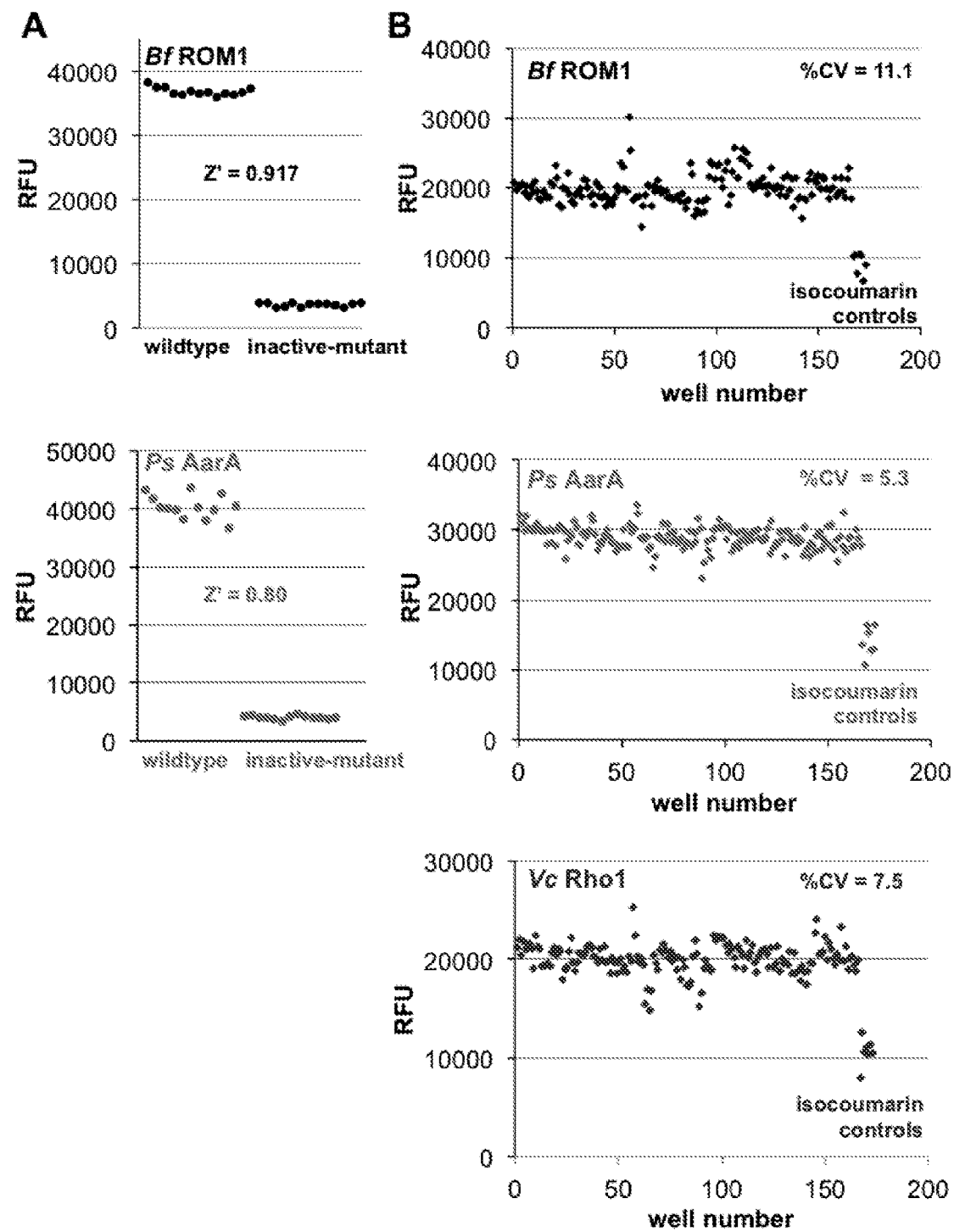
FIG. 12. Assay Evaluation in Manual Compound Screens. A. We calculated Z' scores using wildtype enzyme versus inactive mutant controls because no potent rhomboid inhibitors are available. We did not have the VcRho mutant. B. We assayed 3 different rhomboid proteases independently in hand-pipetted 384-well screens against a custom-assembled library of protease inhibitors, combinatorial compounds, and membrane enzyme inhibitors (all in DMSO). Assays were conducted for 1 hour at 37° C. and fluorescence intensity was read every 2 minutes. Graphed are the 60 minute values, with the last (rightmost) 7 wells being the isocoumarin inhibition controls.

A different strategy would be to neutralize rhomboid immediately before dispensing to the wells (see, e.g., FIG. 12B). This would completely ensure compound stability yet have rhomboid regain proteolytic activity for only moments before being exposed to the compounds. In another embodiment, low pH rhomboid-containing proteoliposomes are delivered directly to compounds pre-dissolved in the neutralizing buffer. The neutral pH buffer preserves compound stability/solubility completely, yet allows for rhomboid activation only as it encounters the compounds.

The present invention also provides an inducible intramembrane protease-substrate system comprising a lipid membrane comprising lipids, the intramembrane protease and a substrate, wherein the system is maintained under acidic or basic conditions to prevent catalysis of the substrate by the protease, and wherein adjusting the pH to physiological conditions allows catalysis of the substrate by the protease. In particular embodiments, the lipids used in the system are a defined set of lipids. Particular defined sets of lipids can be used depending on the protein being studied. In other embodiments, lipid extracts can be used as the lipid source for the reconstituted membrane. Particular lipid extracts—brain lipid extracts, liver lipid extracts, and the like—can be used depending on the protein being studied.

In another aspect, the present invention provides methods of screening for modulators of γ-secretases. In particular embodiments, the present invention provides methods of screening for inhibitors an intramembrane γ-secretase comprising the steps of (a) contacting in a mixture the γ-secretase, a substrate and a γ-secretase inhibitor with a lipid under conditions sufficient to form a membrane comprising the γ-secretase and the substrate; (b) contacting a test agent with the membrane mixture; (c) washing out the γ-secretase inhibitor; (d) assaying substrate cleavage by the γ-secretase; and (e) comparing the assayed substrate cleavage to a reference that does not include the test agent, wherein a decrease of substrate cleavage by the γ-secretase relative to the reference identifies the test agent as an inhibitor of the intramembrane γ-secretase. In certain embodiments, the washing out step is performed, for example, by collecting the membrane by ultracentrifugation and resuspending in inhibitor-free buffer. In particular embodiments, the conditions of step (a) are basic conditions and the method further comprises adjusting the pH to physiological conditions prior to step (d).

In another aspect, the present invention provides methods of screening for modulators of site-2 proteases. A method for identifying inhibitors of an intramembrane site-2 protease comprises the steps of (a) contacting in a mixture the site-2 protease and a substrate with a lipid under conditions sufficient to form a membrane comprising the site-2 protease and the substrate; (b) contacting a test agent with the membrane mixture; (c) adding zinc ions to the mixture; (d) assaying substrate cleavage by the site-2 protease; and (e) comparing the assayed substrate cleavage to a reference that does not include the test agent, wherein a decrease of substrate cleavage by the site-2 protease relative to the reference identifies the test agent as an inhibitor of the intramembrane site-2 protease. In certain embodiments, the contacting step can be performed, for example, in a zinc ion free mixture or with the use of a chelator like phenanthroline or EDTA.

In general, acidic conditions can be used to prevent premature cleavage of the substrate by a protease. In certain embodiments, acetate buffer at pH4 can be used. In specific embodiments, acidic conditions can be used to prevent premature cleavage by a rhomboid protease. In another embodiment, acidic conditions can be used to prevent premature cleavage by a γ-secretase. In yet another embodiment, acidic conditions can be used to prevent premature cleavage by a signal peptide peptidase. In a further embodiment, acidic conditions can be used to prevent premature cleavage by a site-2 protease.

Furthermore, basic conditions can be used to prevent premature substrate cleavage by a protease. In a specific embodiment, basic conditions can be used to prevent premature cleavage by a rhomboid protease. In an alternative embodiment, basic conditions can be used to prevent premature cleavage by a γ-secretase. In another embodiment, basic conditions can be used to prevent premature cleavage by a signal peptide peptidase. Indeed, the pH of the reconstitution conditions can be adjusted—acidic or basic—according to the protease being studied.

The substrate can be any known substrate for the particular intramembrane protease being tested. In certain embodiments, the substrate is a protein. In addition to the TatA and Spitz substrates tested herein, substrates for Rhomboid protease may further include, but are not limited to, PsTatA and EcLacTM2 (both bacterial in origin); ScMgm1 and ScCcp1 (yeast); Spitz, Keren, and Gurken (*Drosophila*); Ephrin-B1,2,3, EGF, TM, and PINK1 (human/mouse); TgAMA1, TgMIC2, TgMIC6, TgMIC8, and TgMIC12 (*Toxoplasma*); PfAMA1, PfEBA175, PfBAEBL, PfJESEBL, PfMAEBL, PfTRAP, PfCTRP, PfMTRAP, and PfRh1,2a,2b,4 (all *Plasmodium*); and parasite lectins, e.g. EHI_044650 (*amoeba*). For site-2 proteases, the substrate can include, but is not limited to, SREBP (TM1)—human/mouse, *Drosophila*, yeast; and PsMucA, EcRseA, BsSpoIVFB, VcTcpP, Cad, iAD1, and iCF10 (all bacterial). For presenilin/γ-secretase, the substrate can include, but is not limited to, APP, Notch, ErbB4, and >50 others known in the art (human/mouse). For signal peptide peptidases (SPPs—related to presenilin), substrate can include, but are not limited to, hepatitis C virus core protein; CMV core and other viral proteins; prolactin signal peptide; HLA signal peptides (human/mouse immune system); and TNF-α.

III. Test Agents: Compound Libraries And Extracts

Potential agonists and antagonists of an intramembrane protease include organic molecules, peptides, peptide mimetics, polypeptides, nucleic acid molecules (e.g., double-stranded RNAs, siRNAs, antisense polynucleotides, aptamers), and antibodies that bind to an intramembrane protease of the present invention and thereby modulate, enhance, activate, increase, decrease, inhibit or extinguish its activity. Potential antagonists also include small molecules that bind to the intramembrane protease thereby preventing binding to cellular molecules with which the intramembrane protease normally interacts, such that the normal biological activity of the intramembrane protease is reduced or inhibited. Small molecules of the present invention preferably have a molecular weight below 2,000 daltons, more preferably between 300 and 1,000 daltons, and most preferably between 400 and 700 daltons. It is preferred that these small molecules are organic molecules.

In general, compounds capable of modulating or altering the biological activity of an intramembrane protease are identified from large libraries of either natural product or synthetic (or semi-synthetic) extracts or chemical libraries according to methods known in the art. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmalMar, U.S. (Cambridge, Mass.).

In one embodiment, test agents of the present invention are present in any combinatorial library known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al., J. Med. Chem. 37:2678-85, 1994); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam, Anticancer. DrugDes. 12:145, 1997).

Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994.

Libraries of compounds may be presented in solution (e.g., Houghten, Biotechniques 13:412-421, 1992), or on beads (Lam, Nature 354:82-84, 1991), chips (Fodor, Nature 364:555-556, 1993), bacteria (Ladner, U.S. Pat. No. 5,223,409), spores (Ladner U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249:404-406, 1990; Cwirla et al. Proc. Natl. Acad. Sci. 87:6378-6382, 1990; Felici, J. Mol. Biol. 222: 301-310, 1991; Ladner supra.).

Those skilled in the field of drug discovery and development will understand that the precise source of a compound or test extract is not critical to the screening procedure(s) of the present invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of an intramembrane protease, variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having modulatory activity. Methods of fractionation and purification of such heterogeneous extracts are known in the art. If desired, compounds shown to be useful agents for the treatment of diseases involving an intramembrane protease are chemically modified according to methods known in the art.

IV. Kits

The present compositions may be assembled into kits for use in evaluation and/or drug screening of intramembrane proteases. Kits according to this aspect of the present invention comprise a carrier means, such as a box, carton, tube or the like, having in close confinement therein one or more container means, such as vials, tubes, ampules, bottles and the like. In certain embodiments, kits can comprise lipids, substrates, proteases, positive controls, negative controls, and the like. In a specific embodiment, a kit comprises (a) lipids for forming a lipid membrane; (b) an acidic solution for mixing the lipids with an intramembrane protease and a substrate; and (c) a solution for adjusting the pH of the mixture to physiological conditions. In another embodiment, the kit further comprises a basic solution for mixing the lipids with an intramembrane protease and a substrate. In another embodiment, the kit further comprises a substrate. The kits of the present invention may also comprise associated instructions for using the present invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Current Protocols in Protein Science"; "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the present invention, and, as such, may be considered in making and practicing the present invention. Particularly useful techniques for particular embodiments will be discussed in the sections that follow.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Protein Purification.

Each HA-rhomboid protein was expressed and purified as described previously (Baker and Urban, 2012; Urban and Wolfe, 2005). Briefly, glutathione-S-transferase (GST) fusion proteins were expressed in *E. coli* C43 (DE3) cells, purified with glutathione-sepharose (GE Healthcare), and eluted by on-column PreScission cleavage to remove the GST tag. Purity of each enzyme was determined by SDS-PAGE stained with Coomassie colloidal blue and quantified on an Odyssey imager (LiCor Biosciences). To avoid erroneous quantitation from inherent differences in Coomassie staining of different rhomboid proteins, all enzymes were standardized by anti-HA analysis in parallel as quantified on an Odyssey imager.

C-terminal Flag-tagged recombinant substrate APP+Spi7-Flag was expressed and purified from *E. coli* as described (Baker and Urban, 2012; Baker et al., 2007). Fluorescein isothiocynate (FITC)-TatA (residues 1-33 of 97) and Spitz (residues 135-168 of 186) substrates containing the entire transmembrane segment were synthesized by Fmoc solid-state chemistry, with FITC conjugated to the N-terminus through a β-alanine linkage, and an amidated C-terminus, and resuspended in 50 mM Tris pH 7.4, 150 mM NaCl, 1 mM DTT, 0.2% (w/v) Sarkosyl. The actual final concentration of each substrate preparation was quantified using FITC fluorescence relative to FITC standards using a Synergy H4 Hybrid plate reader (BioTek).

*E. coli* Liposome Preparation.

100 mg of *E. coli* polar lipid extract in chloroform (Avanti Polar Lipids) was slowly dried into a thin lipid film in a rotary evaporator, and dried under high vacuum overnight on a custom-made glass manifold (Kontes Glass). The film was then resuspended thoroughly in 10 mL of 10 mM HEPES pH 7, 10 mM NaCl, 1 mM DTT, briefly sonicated in a temperature-controlled sonifier (Branson), and extruded through 200 nm pore filters to form liposomes of defined size.

Inducible Reconstitution and Real-Time Proteolysis Assay.

30 μg of *E. coli* liposomes were mixed with 50 mM NaAcetate pH 4.0, 150 mM NaCl, 0.05 to 500 pmoles of rhomboid enzyme, and 20 to 1600 pmoles of FITC-substrate. This co-reconstitution mix was diluted 20-fold with 12.5 mM NaAcetate pH 4.0, 37.5 mM NaCl to reduce detergent below its critical micelle concentration and promote reconstitution. Proteoliposomes were collected by ultracentrifugation at 600,000 g for 20 minutes in an Optima MAX-XP ultracentrifuge (Beckman). The supernatant was removed by aspiration, the pellet resuspended in 50 mM Tris pH 7.4, 150 mM NaCl, 1 mM DTT to initiate proteolysis (in the presence of $D_2O$ for isotope experiments), rapidly transferred into a pre-warmed black 384-well microtiter plate, covered with film to prevent evaporation, and incubated at 37° C. in a Synergy H4 Hybrid plate reader (BioTek). Fluorescence was monitored every minute using monochromators set to wavelengths of 485±20 nm (excitation) and 528±20 nm (emission). Alternatively, time points were quenched with equal volumes of 2× Tricine SDS-sample buffer, resolved on 16% Tricine gels (Life Technologies), and imaged with a blue laser and fluorescein emission filters on a Typhoon Imager (GE Healthcare). APP+Spi7-Flag and HA-EcGlpG were co-reconstituted as above, resolved by SDS-PAGE, detected by 2-color anti-Flag and anti-HA western analysis, and imaged with an Odyssey infrared scanner (LiCor Biosciences).

In Vivo TatA-Flag Titration.

Expression of TatA-Flag (full-length protein with a C-terminal Flag tag) in log-phase *E. coli* K12 BW25113 cells was titrated using arabinose-mediated induction from a pBAD plasmid. Induced cultures were grown at 37° C. in a shaking incubator for 2 hours. Cleavage by endogenous GlpG was quantified by resolving cell lysates on a 16% Tricine SDS-polyacrylamide gel, followed by anti-Flag western analysis and imaging with an Odyssey infrared scanner (LiCor Biosciences). To quantify expression levels of TatA-Flag, cells were lysed in a French pressure cell (2 passes at 16,000 PSI), and the lysate was clarified to remove unbroken cells at 9,000 g for 8 minutes in a JLA 8.1000 rotor (Beckman). Membranes were collected by ultracentrifugation at 50,000 rpm for 1 hour in a MLA-55 rotor (Beckman). Peripheral and contaminating soluble proteins were removed with a sodium carbonate wash. Total membrane protein from each titration were separated on a 4-20% tris-glycine SDS-polyacrylamide gel, stained with a colloidal Coomassie blue dye (LiCor Biosciences), and quantified with an Odyssey infrared scanner. TatA-Flag expression was converted to molar ratio of membrane proteins by correcting signals for molecular weight, then converted to mole % of membranes. To estimate $k_{cat}$ in vivo, endogenous Flag-EcGlpG levels in membranes prepared by sucrose gradient ultracentrifugation were quantified by western analysis relative to purified Flag-EcGlpG as a standard.

Fitting and Statistical Analysis.

All data were analyzed and graphed using the R language and environment. Initial rates were extracted from real-time curves between 4 and 14 minutes using the slope (m) in a linear model: y=mx+b. Initial rates versus substrate concentration of reconstituted reactions were modeled using the Hill-modified Michaelis Menten equation: $v_0 = (V_{max} * [S_0]^h)/(K_m^h + [S_0]^h)$. Importantly, we did not observe cooperativity with reconstituted reactions analyzed by SDS-PAGE, indicating that cooperativity is not a true feature of the enzyme reaction. P-values in pairwise comparisons were derived from multiple non-linear regression analysis and $k_{cat}$ p-values were corrected for multiple comparisons using the Bonferroni method ($K_M$ p-values were not corrected because none achieved significance).

Results

Development of an Inducible Co-Reconstitution System.

In order to study kinetics of proteolysis directly within the membrane, we faced three obstacles that are inherent to GlpG and substrate both being transmembrane proteins. First, although membrane proteins are prone to aggregation in vitro, an important requirement for kinetic analysis is that enzyme concentration does not change during the course of the reaction. We evaluated this concern and found no loss in activity upon pre-incubating E. coli GlpG at 37° C. for 1 hour prior to initiating the reaction (FIG. 1A), revealing GlpG enzyme preparations are robust for kinetic analysis.

Figure 1C:
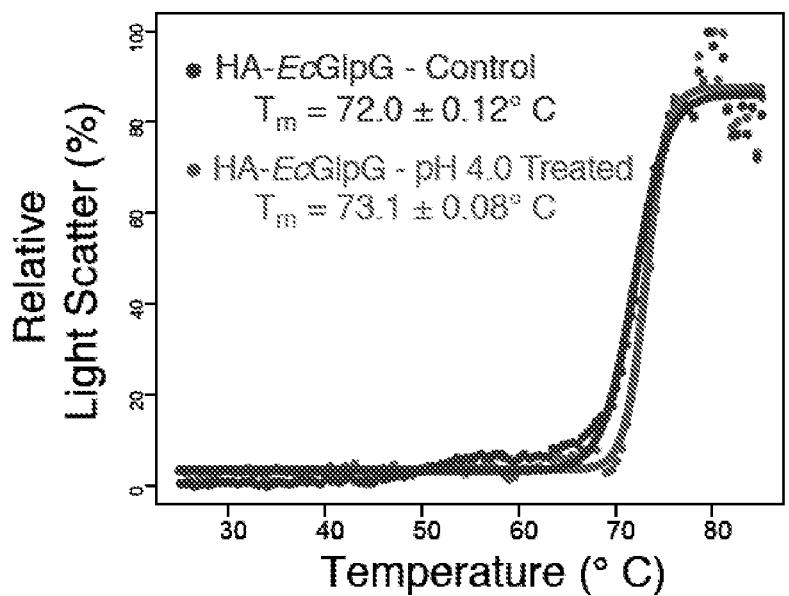
Figure 1D:
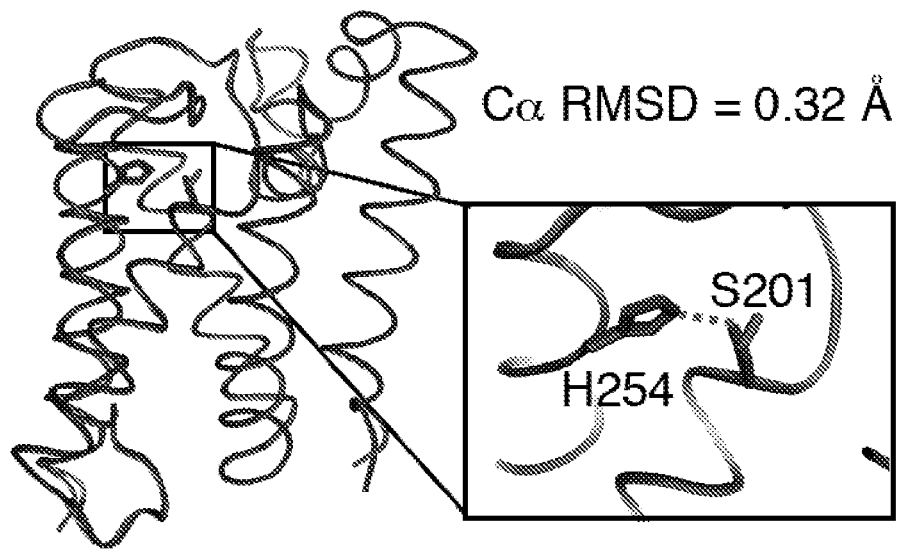

The greatest challenge to kinetic analysis of proteolysis within membranes is that cleavage already begins during the lengthy procedure to reconstitute protease and substrate into the membrane (Osenkowski et al., 2008). To overcome this obstacle, we developed a rapid and reliable co-reconstitution method in which proteolytic activity can be switched off and on. We reasoned that co-reconstituting at lower pH would protonate the catalytic histidine, rendering it catalytically inactive. Then, after collecting the proteoliposomes by ultra-centrifugation, we planned to initiate the reaction by raising the pH to the physiological 7.4. Under these conditions, we detected no proteolysis during the lowered pH co-reconstitution, and regained full protease activity relative to untreated controls upon neutralization (FIG. 1B). Moreover, treated GlpG was indistinguishable from untreated GlpG in a sensitive and quantitative structural stability assay (Baker and Urban, 2012), arguing that the pH switch did not alter enzyme structure (FIG. 1C). In fact, crystallization of GlpG at neutral and low pH revealed its overall architecture was unperturbed (Cα RMSD of ~0.32 Å), yet at low pH the serine sidechain was incompetent for catalysis because it had turned away from the histidine (FIG. 1D and Table 1), which is consistent with histidine protonation.

TABLE 1

Crystallographic Statistics

| | GlpG-pH 7.5 | GlpG-pH 4.5 |
|---|---|---|
| Data collection | | |
| Space group | R32 | R32 |
| Unit cell dimensions | | |
| a, b, c (Å) | 110.6, 110.6, 127.7 | 110.7, 110.7, 127.8 |
| α, β, γ (°) | 90, 90, 120 | 90, 90, 120 |
| Resolution (Å) | 50.0-2.17 | 50.0-2.28 |
| | (2.21-2.17)[a] | (2.32-2.28)[a] |
| Observations | 103,835 | 107,735 |
| Unique reflections[a] | 29,338 (952) | 26,208 (1617) |
| Redundancy | 3.5 (1.6) | 4.1 (3.3) |
| I/σI | 13.8 (1.9) | 8.3 (2.2) |
| Completeness (%)[a] | 99.5 (62.5) | 99.7 (70.6) |
| $R_{merge}$ (%)[a,b] | 6.2 (54.2) | 11.5 (55.3) |
| Refinement | | |
| Resolution (Å) | 50.0-2.4 | 50.0-2.3 |
| | (2.46-2.40)[a] | (2.36-2.30)[a] |
| No. of reflections | 9,925 | 9,394 |
| $R_{work}/R_{free}$ | 0.187/0.244 | 0.199/0.251 |
| | (0.179/0.282)[a] | (0.259/0.347)[a] |
| No. of atoms | 1502 | 1472 |
| Protein residues | 1452 | 1452 |
| Water molecules | 50 | 20 |
| Average B factors (Å$^2$) | 43.5 | 44.4 |
| Protein | 43.2 | 44.6 |
| Water | 53.4 | 36.5 |
| RMSD | | |
| Bonds (Å) | 0.017 | 0.019 |
| Angles (°) | 1.75 | 1.92 |

[a]Values in parentheses correspond to highest resolution shell.
[b]$R_{merge} = (\Sigma|I(i) - <I(h)>|/\Sigma I(i))$.
[c]$R_{work} = \Sigma|F_o - F_c|/\Sigma F_o$.
[d]$R_{free}$ was calculated over reflections in a test set not included in atomic refinement: GlpG-pH 7.5, 4.9%; GlpG-pH 4.5, 5.2%.

Quantitative Analysis of Intramembrane Proteolysis in Real Time.

Figure 2A:
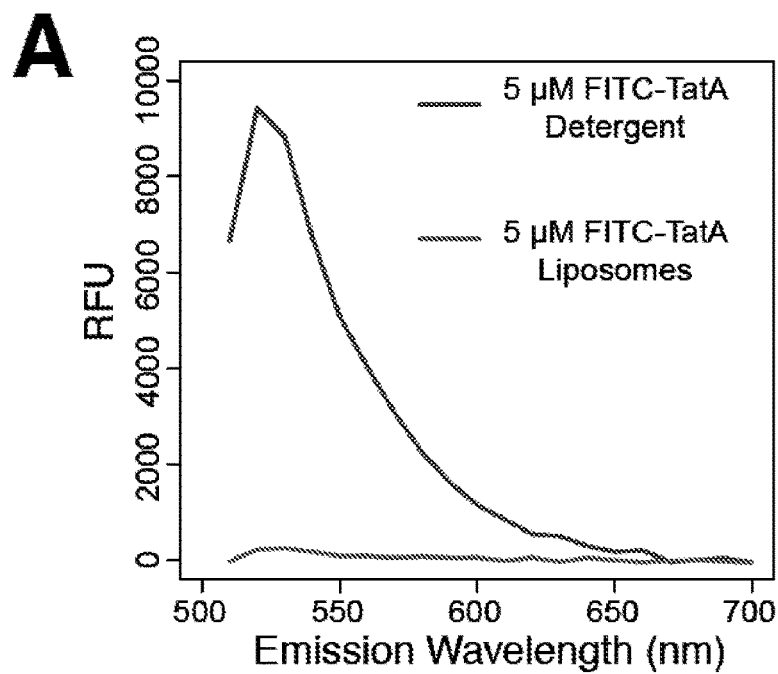
FIG. 2. Quantifying proteolysis within the membrane in real time. (A) FITC-TatA fluorescence is quenched in proteoliposomes (red), but not in detergent micelles (blue). Shown is an emission scan: see FIG. 8 for absorption/excitation scans. (B) Assay schematic: transmembrane FITC-TatA and HA-EcGlpG in detergent were co-reconstituted into proteoliposomes at pH 4 (red shading), collected by ultracentrifugation, and proteolysis initiated by neutralization (blue shading). Proteoliposomes quench fluorescence, which is relieved by cleavage-mediated release. (C) Real-time progress curves at 37° C. (read/minute) of EcGlpG reconstituted with indicated FITC-TatA concentrations (mole % relative to phospholipids). Mutating EcGlpG or TatA, or pretreating with JLK6, abrogated signal to background. (D) Fluorescence scan of gel analysis confirmed linear product accumulation (top $R^2$=0.997), and sensitivity to mutation/inhibition. Also see FIG. 9B for gel analysis of extended incubations. Lower gel and graph indicate that the TatA construct lacking the FITC label was not cleaved more efficiently. (E) MALDI-TOF analysis of the N-terminal FITC-TatA cleavage product (red arrow indicates cleavage site).
Figure 2B:
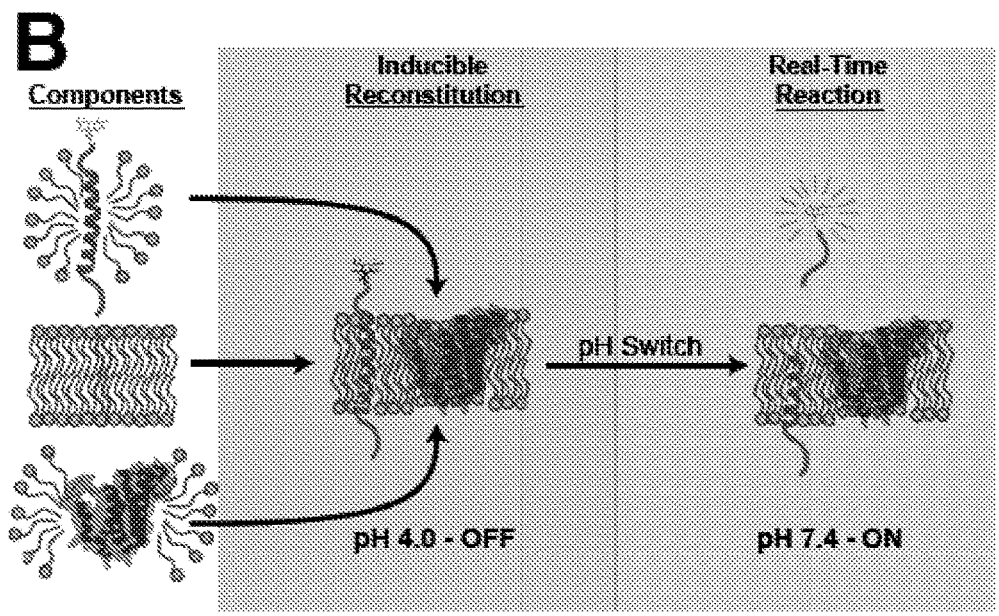
Figure 2C:
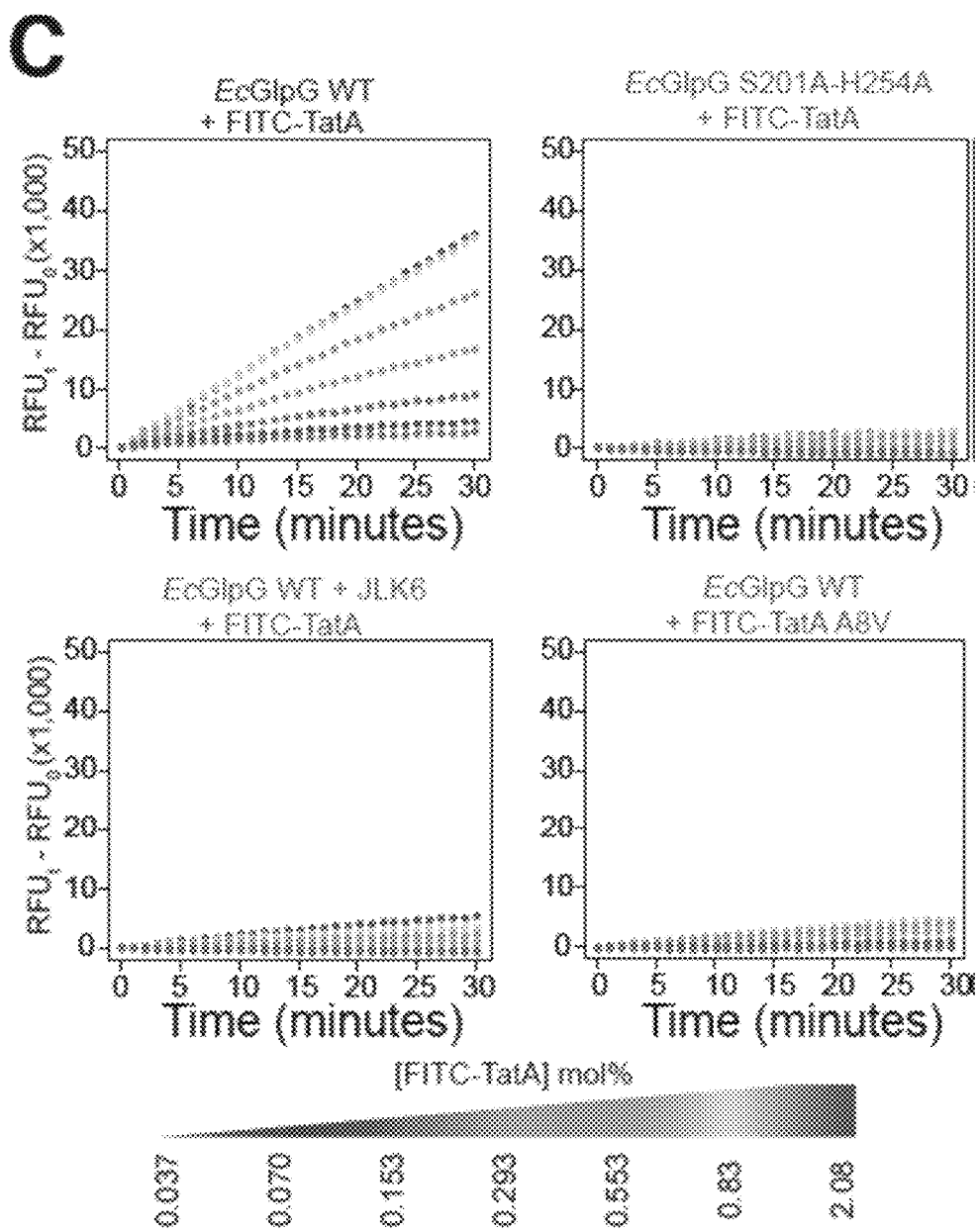
Figure 2D:
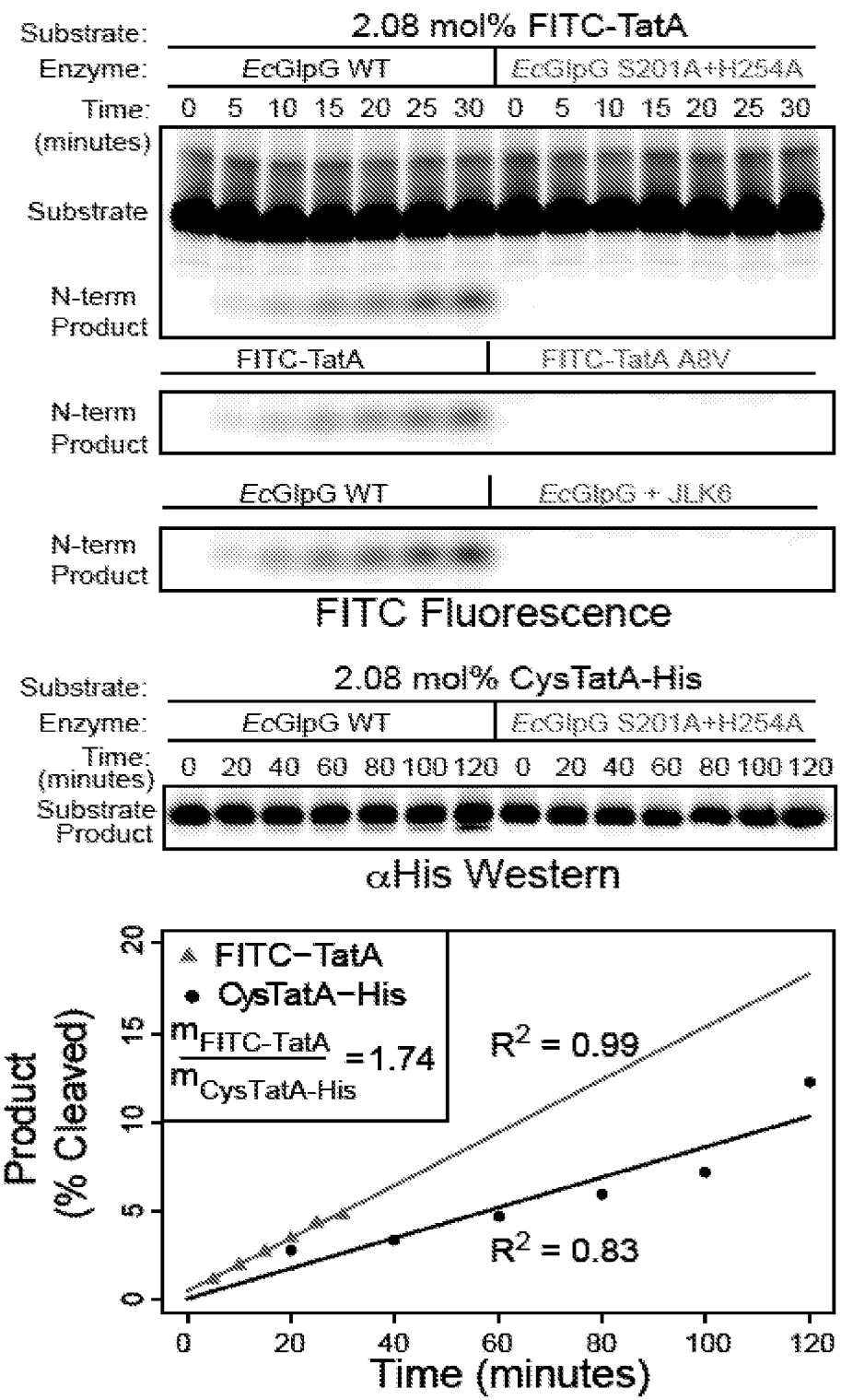
Figure 2E:
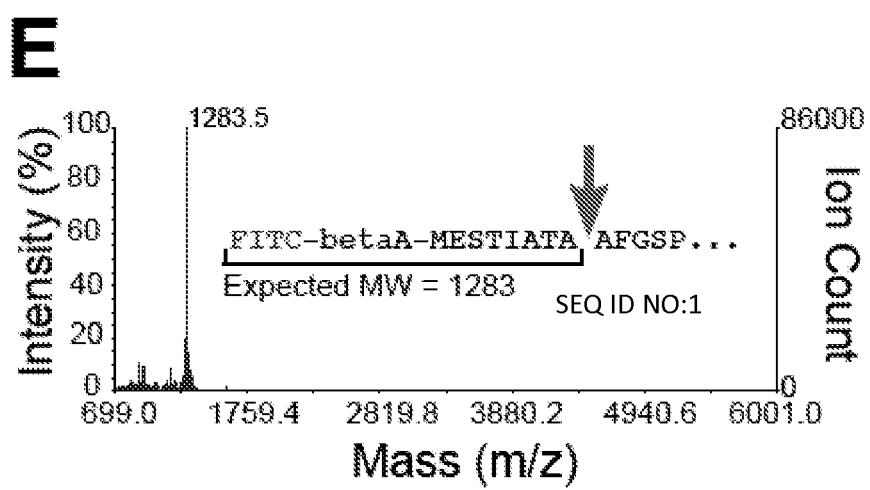
Figure 8A:
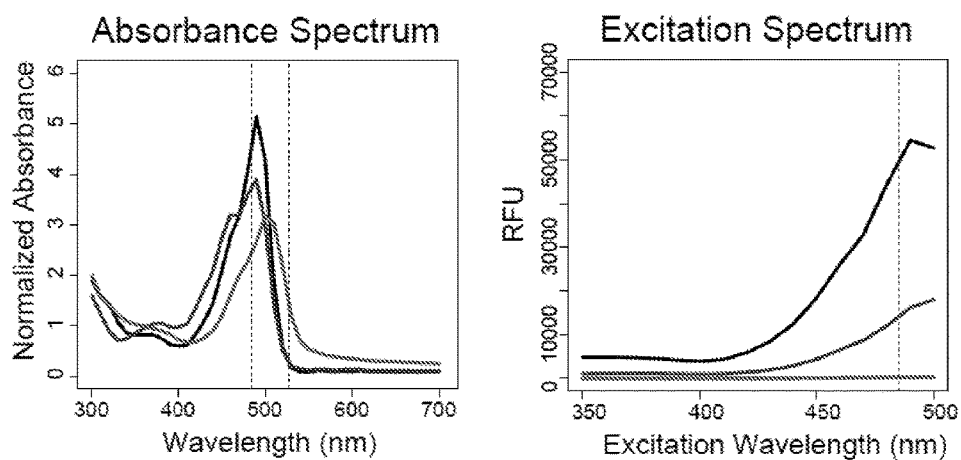
FIG. 8. (A) Fluorescence of FITC-TatA was quenched in proteoliposomes (red), but not in detergent micelles (blue). FITC-TatA in proteoliposomes maintained the ability to absorb (left panel), but failed to fluoresce over a range of excitation and emission wavelengths (middle and right panel, blue dashed line=485 nm, green dashed line=528 nm). (B) Circular dichroism analysis of FITC-TatA reconstituted in *E. coli* lipids showed that FITC-TatA adopts a helical secondary structure.
Figure 8B:
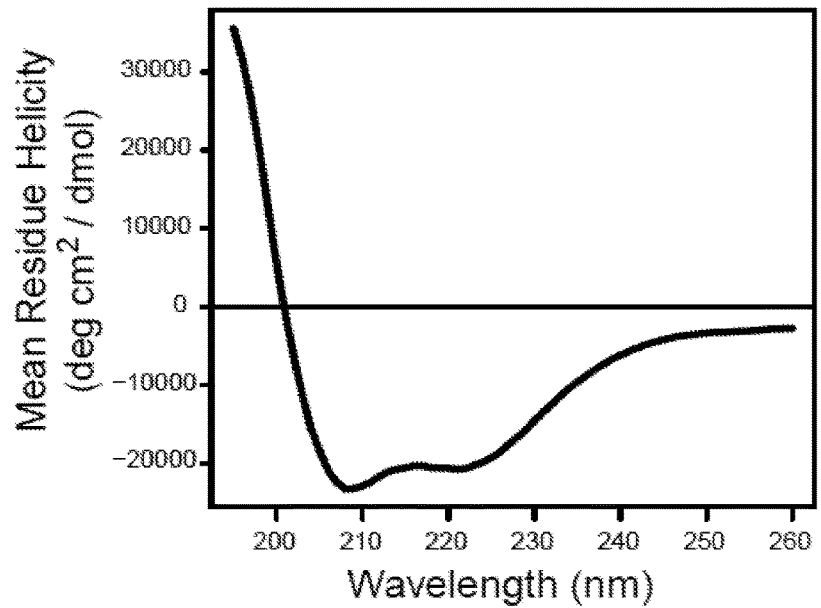

With robust enzyme preparations and this novel reconstitution method established, we next focused on developing a substrate that would permit monitoring intramembrane proteolysis in real time. Unexpectedly, we discovered that a FITC fluorophore attached to the natural amino-terminus of a Providencia stuartii TatA construct, the only known bacterial rhomboid substrate (Stevenson et al., 2007), was robustly quenched when reconstituted into proteoliposomes composed of E. coli lipids (FIGS. 2A, 2B and S1A). In the presence of GlpG, however, a fluorogenic signal was generated at a rate (FIG. 2C) that was perfectly coincident with appearance of the cleaved product as assessed by tricine gel analysis (FIG. 2D). Mass spectrometric analysis confirmed TatA was being cut only at the natural rhomboid cleavage site between alanines 8 and 9 (Stevenson et al., 2007) (FIG. 2E). Importantly, both fluorescence and the cleaved product were absent when we mutated either the substrate at the alanine preceding the cleavage site, or the GlpG catalytic residues (FIGS. 2C and 2D). JLK6, an isocoumarin-based rhomboid inhibitor (Vinothkumar et al., 2010), blocked generation of the fluorescence signal and cleavage product (FIGS. 2C and 2D). Finally, the FITC moiety neither reduced proteolysis (FIG. 2D), nor affected the helicity of TatA in membranes as measured by circular dichroism (FIG. 8B). Therefore, FITC-TatA cleavage exhibits all known hallmarks of rhomboid intramembrane proteolysis, and permits its monitoring within the membrane in real-time.

Steady-State Kinetic Analysis of Proteolysis within the Membrane.

Figure 3A:
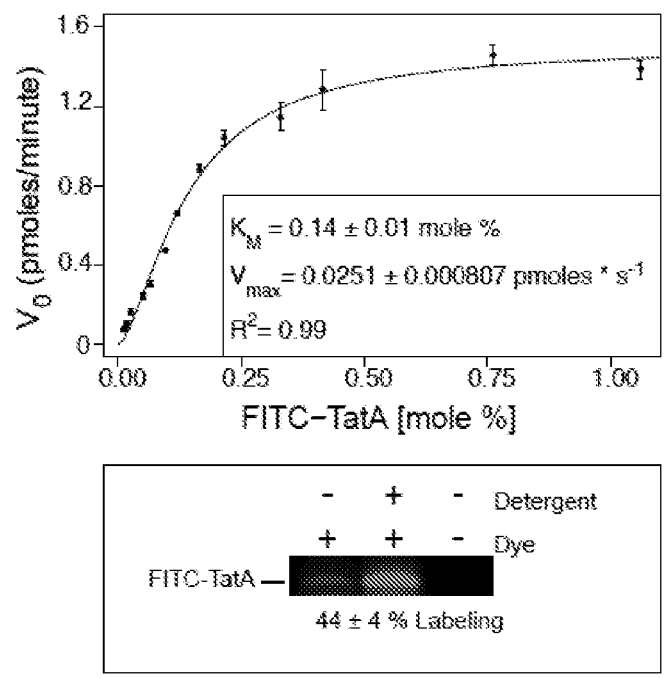
FIG. 3. Intramembrane proteolysis kinetics and equilibrium binding parameters inside the membrane. (A) Real-time kinetics of FITC-TatA cleavage by EcGlpG in proteoliposomes was fit with a Michaelis-Menten model (mean±sem, n=2, inset: fit±sd). Gel image (below) quantifying FITC-TatA-Cys labeling by a membrane-impermeable thiol-reactive dye, revealing half of TatA reconstituted with its amino-terminus facing the liposome interior. The reconstitution efficiency was consistent between experiments (see FIG. 9A). Reactions were also analyzed on 16% tricine gels, products quantified and plotted (see FIG. 9C). (B) Binding of FITC-TatA to catalytically inactive TMR-GlpG (C104A+W196TMR+H254A) in proteoliposomes. Plotted is background-subtracted FRET fluorescence intensity versus mole fraction of FITC-TatA (relative to phospholipids). $K_a$ was derived from the curve fit. (C) Mass spectra of EcGlpG incubated with the activity-based inhibitor JLK6 produced a complete mass shift, revealing all purified EcGlpG is active. (D) TatA-Flag cleavage in *E. coli* cells by endogenous GlpG. TatA expression levels were titrated with arabinose, and cleavage assessed by anti-Flag western blot (upper gel). Deleting genomic GlpG (ΔGlpG) resulted in no cleavage. Levels of endogenous GlpG (Flag-tagged by knock-in) were quantified in duplicate relative to known Flag-GlpG pure protein standards by anti-Flag western blot (lower gel). Cross-reactive bands served as loading controls. Graph: half maximal cleavage by endogenous GlpG occurred when TatA reached 0.19 mole percent (relative to phospholipids). Also shown (inset) is a Coomassie blue-stained SDS-PAGE gel revealing TatA became 20% of the *E. coli* membrane proteome when induced with 1 mM arabinose (also see FIG. 9D).
Figure 9A:
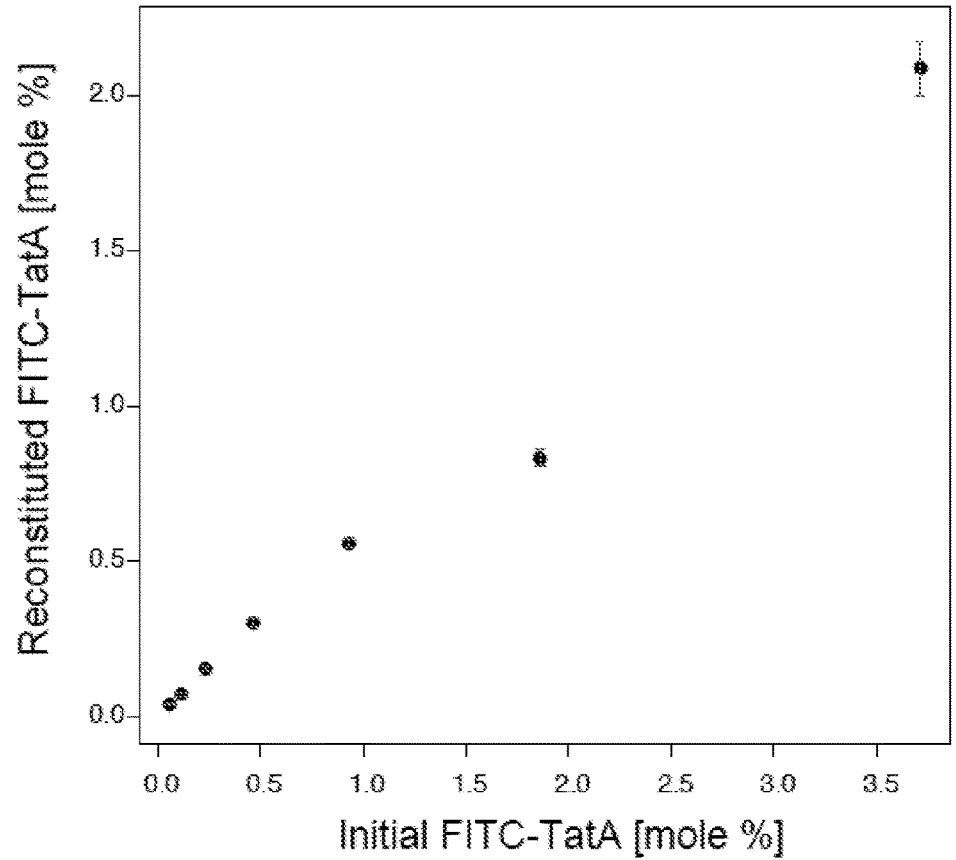
FIG. 9. (A) Reconstitution efficiency of FITC-TatA into proteoliposomes quantified by fluorescence was very consistent (mean±sem, n=14). (B) Extended incubation of FITC-TatA cleavage with HAEcGlpG revealed the majority of substrate was turned over. Shown is a fluorescence scan of a 16% tricine gel. (C) A Michaelis-Menten (inset: fit±sd) model fitted to data derived from a 40-minute reaction of HA-EcGlpG cleavage of FITC-TatA analyzed by SDS-PAGE on a 16% tricine gel (lower image). No cooperativity was observed in the gel-analyzed fit. (D) Coomassie stained gel of titrated TatA-Flag membrane preparations. TatA-Flag (arrow) accumulates to ~20% of all membrane proteins. The asterisk denotes a background band co-migrating with TatA-Flag, the signal of which was subtracted from the TatA-Flag signal.
Figure 9B:
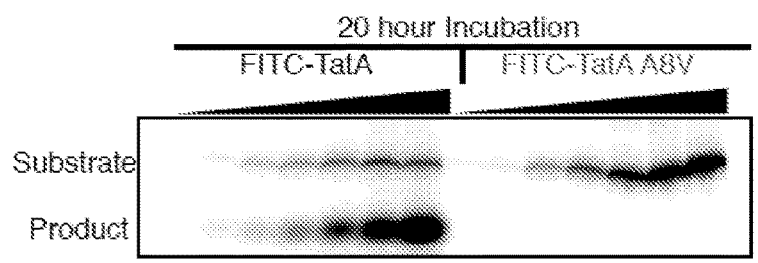

To establish controlled conditions for a Michaelis-Menten kinetic system, we lowered GlpG levels to 4 pmoles while varying substrate from 20 to 1600 pmoles and co-reconstituted both into 200 nm proteoliposomes comprised of E. coli lipids to preserve its physiological environment as much as possible (FIG. 9A). Under these low enzyme conditions, <5% of the substrate was converted to product in 30 minutes (FIG. 2D), thus satisfying Michaelis-Menten requirements of constant substrate concentrations. Progress curves remained linear for ~60 minutes before the reactions expectedly slowed due to substrate depletion and product accumulation. Extended incubation times allowed FITC-TatA turnover (FIG. 9B), arguing that >85% of the substrate is available to the protease. Finally, FITC-TatA reconstituted in both orientations in approximately equal proportions, as quantified by reacting single engineered cysteines with membrane-impermeable dyes (FIG. 3A). As such, the effective concentration of FITC-TatA per orientation is half of the total amount reconstituted.

Figure 3B:
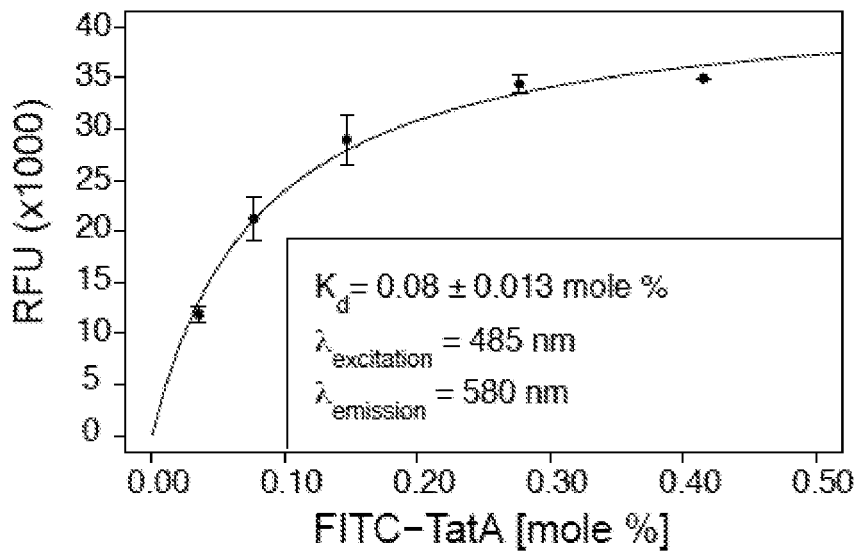
Figure 9C:
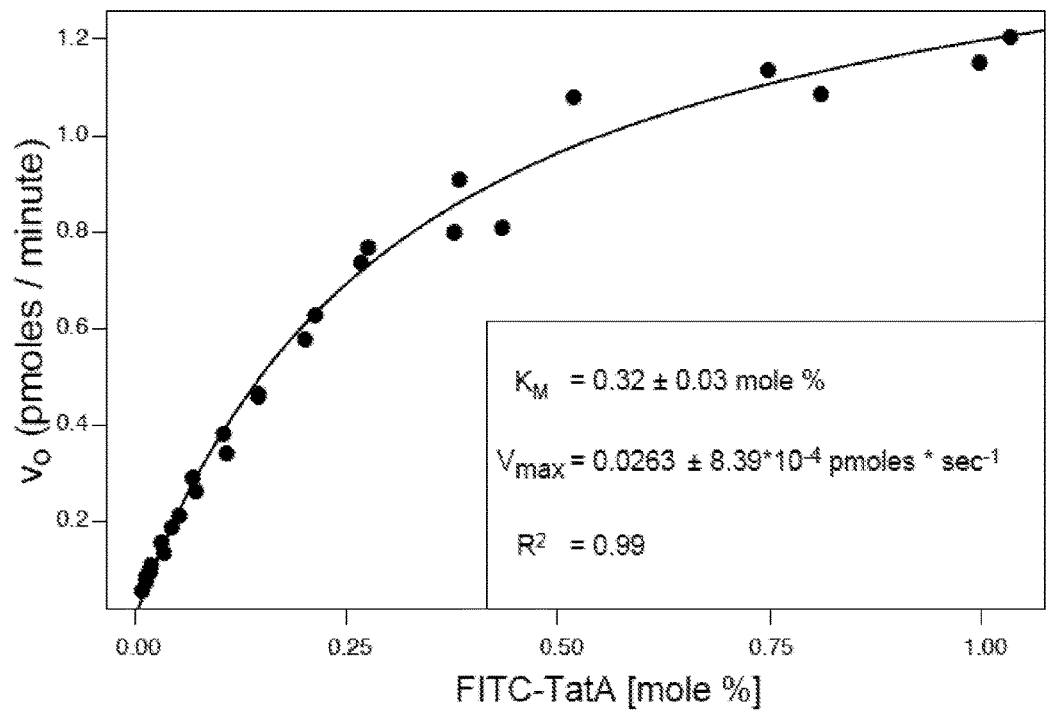
Figure 9C:
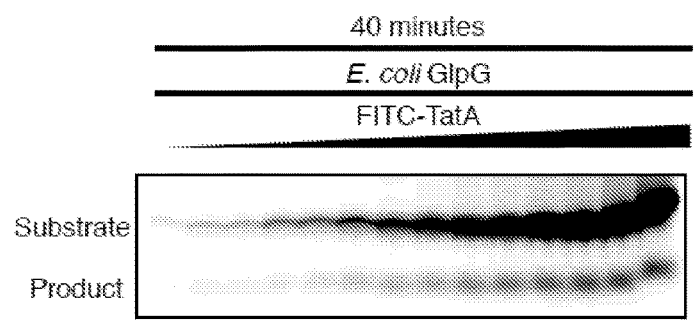

Plotting the substrate concentration versus reaction velocity (measured over the first 15 minutes) produced a rectangular hyperbola that could be fit exceptionally well ($R^2=0.99$) with a Michaelis-Menten equation (FIG. 3A). Remarkably, the resulting data revealed an extraordinarily high $K_M$ of 0.14±0.02 mole percent relative to phospholipid (~1 substrate transmembrane segment per 350 monolayer phospholipids). We verified this measurement independently by tricine gel analysis (FIG. 9C). However, since $K_M$ is more complex than physical affinity alone, we developed a binding assay to measure the $K_d$ between rhomboid and substrate within the membrane directly. We installed a tetramethylrhodamine (TMR) FRET acceptor group onto an extracellular GlpG loop at a site we previously found does not perturb protein structure (Baker and Urban, 2012). Co-reconstituting different amounts of FITC-TatA resulted in an increasing FRET signal from a catalytically-inactive mutant of TMR-GlpG that became saturated, revealing an apparent $K_d$ of 0.08±0.026 mole percent (FIG. 3B), which agrees well with the low affinity revealed by kinetic analysis.

Figure 3C:
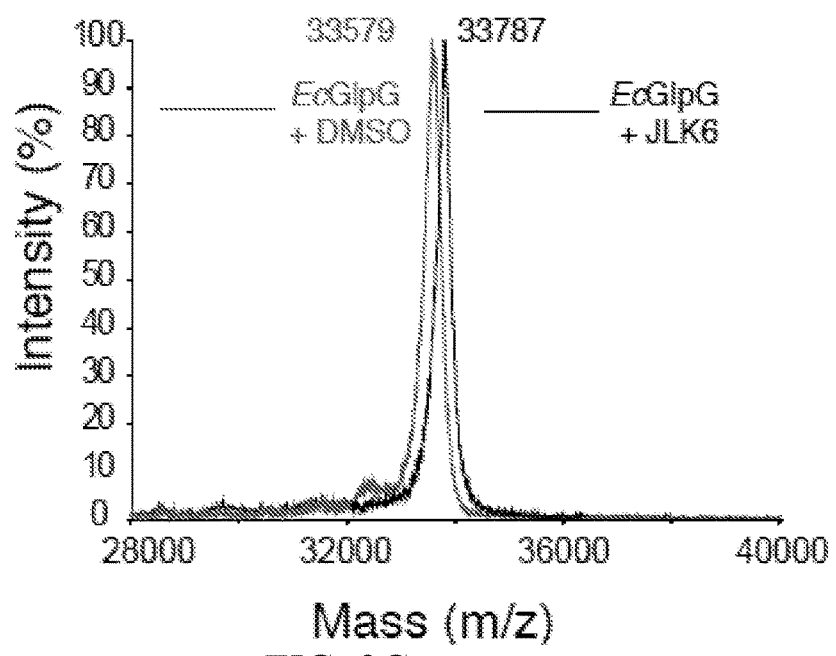

To derive the catalytic turnover rate, $k_{cat}$, from the measured $V_{max}$, we quantified the fraction of active protease in our preparations by incubating with JLK6, which is a 'suicide inhibitor' that covalently labels only active GlpG (Vinothkumar et al., 2010). Mass spectrometry revealed that ~100% of GlpG in our preparations is catalytically active (FIG. 3C), yielding a $k_{cat}$ of 0.0063±0.00021 cuts per second ($s^{-1}$), or >2.5 minutes required for a single cleavage event within the membrane when the enzyme is saturated with substrate.

Evaluation of Intramembrane Protease Kinetics in Living Cells.

Figure 3D:
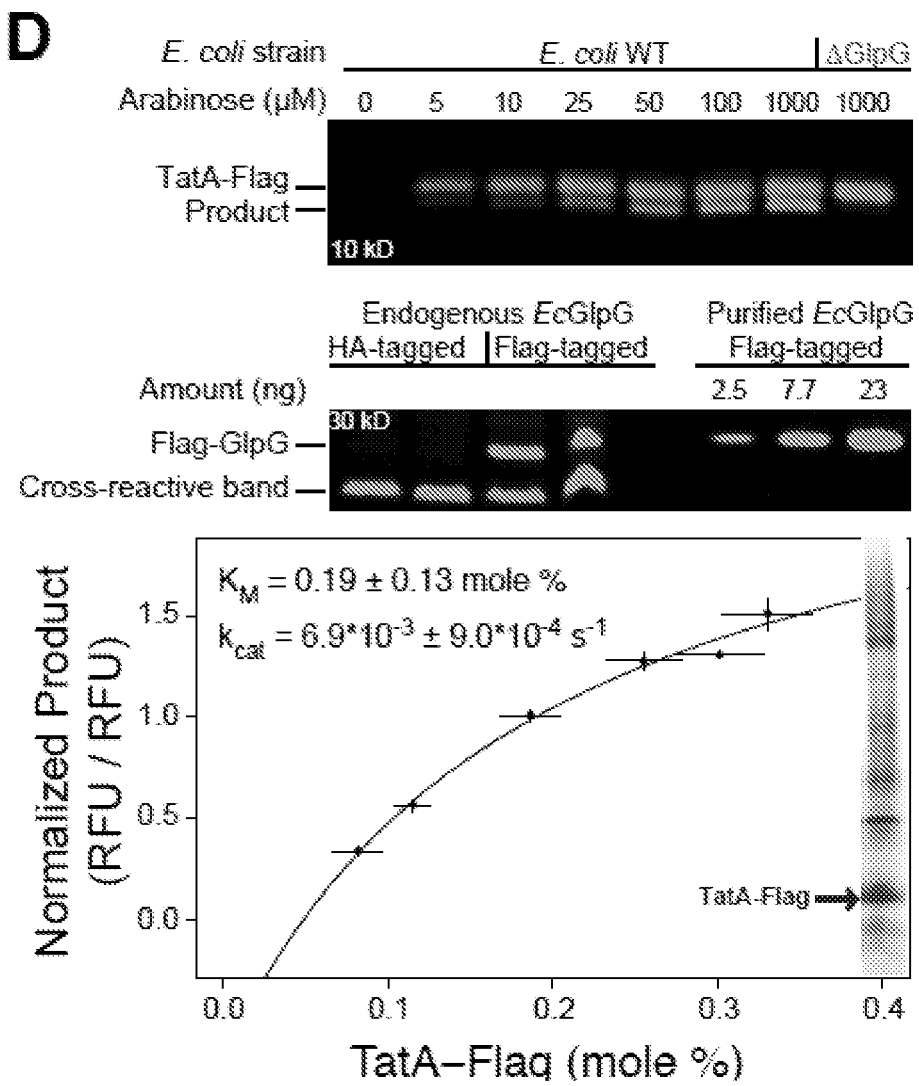
Figure 9D:
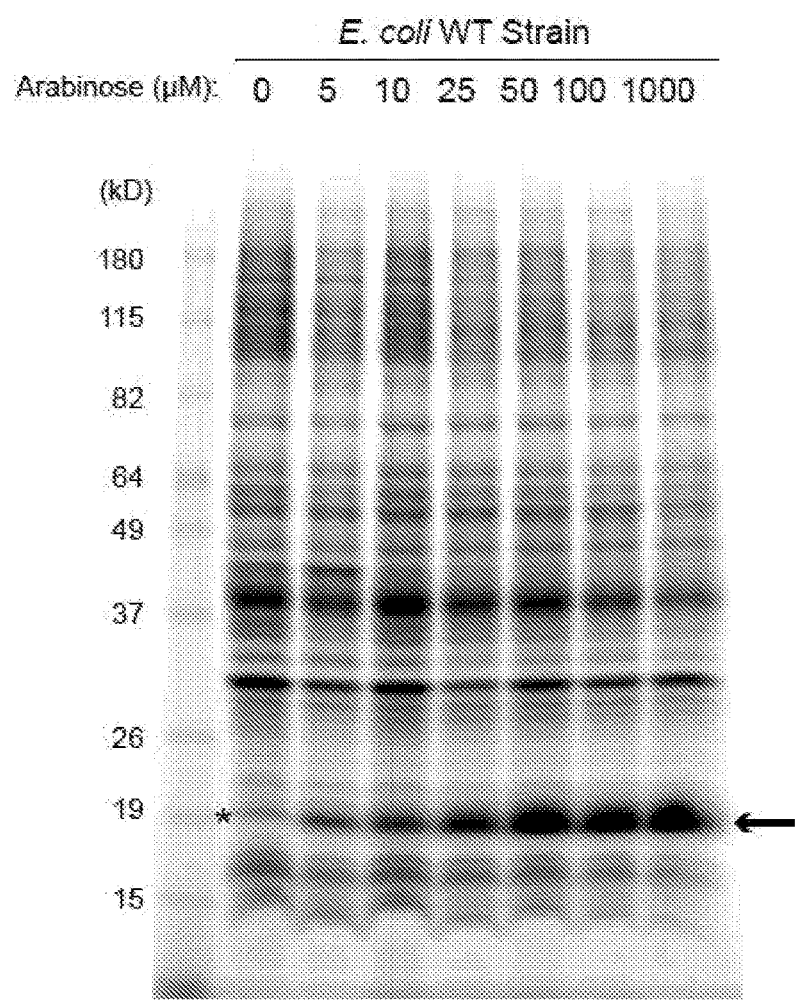

The kinetic parameters governing proteolysis within the membrane were unexpectedly inefficient, raising the concern that our reconstitution system may be missing an unknown component, or may not accurately reflect physiological conditions. In fact, while we have been careful to use lipids purified from growing *E. coli* cell for forming our liposomes, in vitro membrane systems cannot recapitulate potential bilayer asymmetry of lipids, or potential crowding induced by 'bystander' proteins, that may be present in natural membranes. We therefore examined the characteristics of rhomboid proteolysis directly in living *E. coli* cells by expressing full-length TatA from an arabinose promoter that allows titration of target protein levels. Using this system we achieved TatA levels ranging from undetectable to becoming the most abundant protein in the cell membrane (FIG. 9D). As expected, increasing TatA resulted in increased intramembrane proteolysis by endogenous GlpG in the natural membranes of living *E. coli* cells (FIG. 3D). Cleavage was absent in GlpG knockout cells. Remarkably, even when TatA became the most abundant protein in the cell, GlpG was not yet saturated with substrate, confirming low substrate binding affinity. Quantifying TatA levels and cleavage yielded a Michaelis-Menten-like curve, with an 'apparent in vivo' $K_M$ of 0.19 mole percent, which is remarkably similar to 0.14 mole percent that we measured in our in vitro reconstitution system.

We also estimated the proteolytic rate in vivo by epitope tagging endogenous GlpG in the *E. coli* chromosome. This was critical because if we overexpressed GlpG even slightly we could titrate out any potential stimulatory cofactor or condition. Quantification of endogenous GlpG levels relative to pure protein standards (FIG. 3D) yielded an 'apparent in vivo' $k_{cat}$ of 0.0069±0.0009 $s^{-1}$, which again was remarkably similar to 0.0063±0.00021 $s^{-1}$ that we measured in our reconstitution system. As such, GlpG exhibits low affinity for substrate and slow catalytic rate even in living cells, validating that our reconstitution system faithfully recapitulates physiological conditions for GlpG proteolysis.

The Membrane Environment Slows Rhomboid Proteolysis.

Figure 4A:
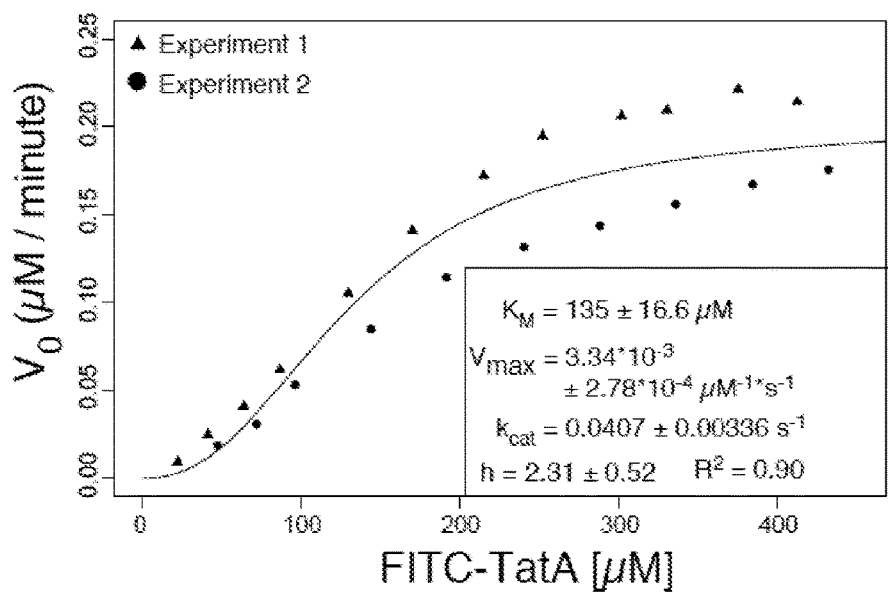
FIG. 4. Intramembrane proteolysis kinetics and equilibrium binding analyzed in 3-dimensions. (A) Michaelis- Menten plot of FITC-TatA cleavage by HA-EcGlpG in detergent micelles (inset: fit±sd). Variation increased at >100 μM due to variable solubility of the transmembrane substrate. (B) Analysis of FITC-TatA coprecipitation with the inactive mutant His-EcGlpG C104A+H254A. Quantification revealed <0.1% of FITC-TatA eluting with His-EcGlpG, which under non-equilibrium conditions corresponds to an apparent $K_d \geq 1$ mM. (C) HPLC gel filtration analysis of FITC-TatA mixed with HA-EcGlpG S201A+H254A reveals a small complex peak (arrow), which is absent in the elution profile of FITC-TatA alone. The single $A_{280}$ (protein absorption) peak is an overlap of HA-EcGlpG (eluting first) and FITC-TatA (right shoulder). (D) HPLC equilibrium gel filtration analysis of FITC-TatA/EcGlpG (inactive S201A+H254A mutant) complex versus FITC-TatA/BSA control run on a column equilibrated with 9.5 μM FITC-TatA. The $A_{485}$ (FITC absorption) peak corresponds to the GlpG-TatA complex, while the trough results from FITC-TatA depletion from the mobile phase due to GlpG binding (peak/trough absence with BSA indicates no binding).

Having discovered that the kinetics of proteolysis within the membrane are inefficient, we sought to test whether this reflects limitations imposed by the membrane environment. We examined proteolysis in detergent micelles that support high rhomboid activity, and found a strikingly high $K_M$ of at least 135±16.6 μM, with $V_{max}$ approached at >300 μM substrate (FIG. 4A). The $V_{max}$ we measured is ~10 times faster than previously measured for rhomboid proteases in detergent (Lazareno-Saez et al., 2013), suggesting that prior studies did not saturate enzyme with substrate but instead suffered plateauing for another reason, such as substrate aggregation at higher concentrations and extended incubation times of 2 hours.

Figure 4B:
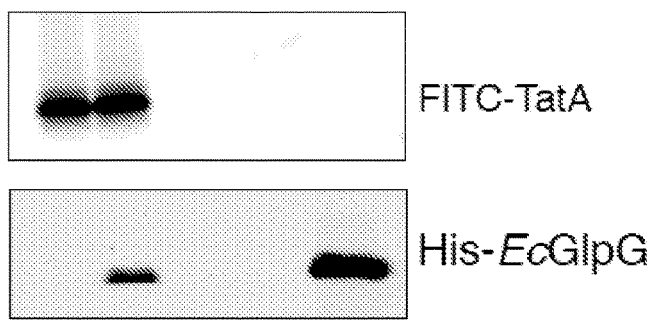
Figure 4C:
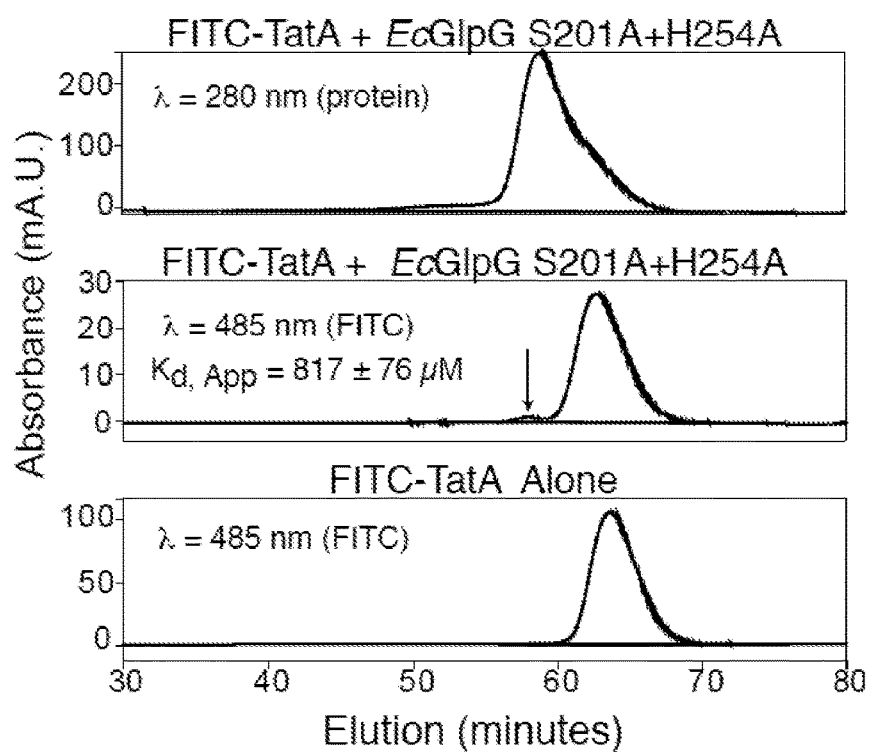
Figure 4D:
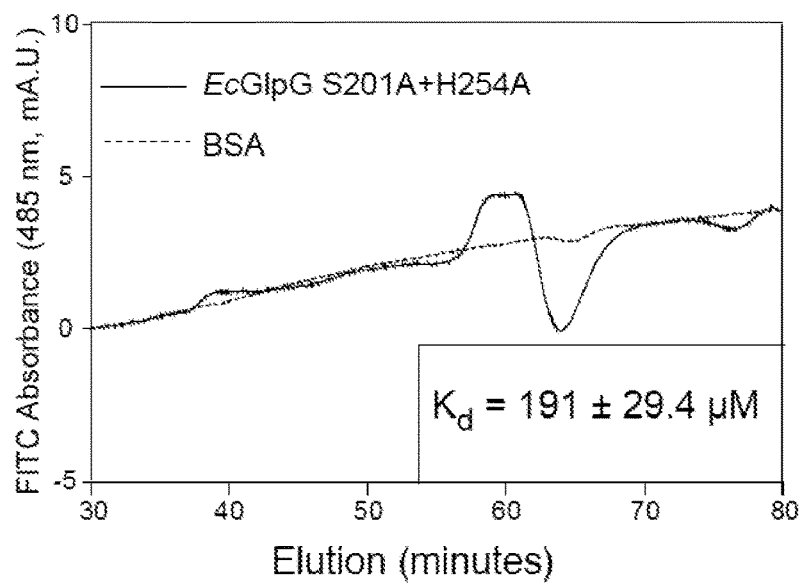

A way to distinguish between indirect effects and true binding is to measure the $K_d$ directly between rhomboid and substrate, which has never been achieved for any intramembrane protease. Commonly used gel filtration and co-precipitation approaches indicated low affinity of >800 μM (FIGS. 4B and 4C). Since these approaches separate complex from monomers, they promote dissociation and thus can over-estimate $K_d$. We therefore performed equilibrium gel filtration (Hummel and Dreyer, 1962) by pre-equilibrating the entire column with substrate. Under these equilibrium conditions, the $K_d$ between rhomboid and substrate was 191±29.4 μM (FIG. 4D), which is in excellent agreement with our measured $K_M$. These values indeed suggest that rhomboid does not display even modest natural affinity for substrates in any environment.

Figure 5A:
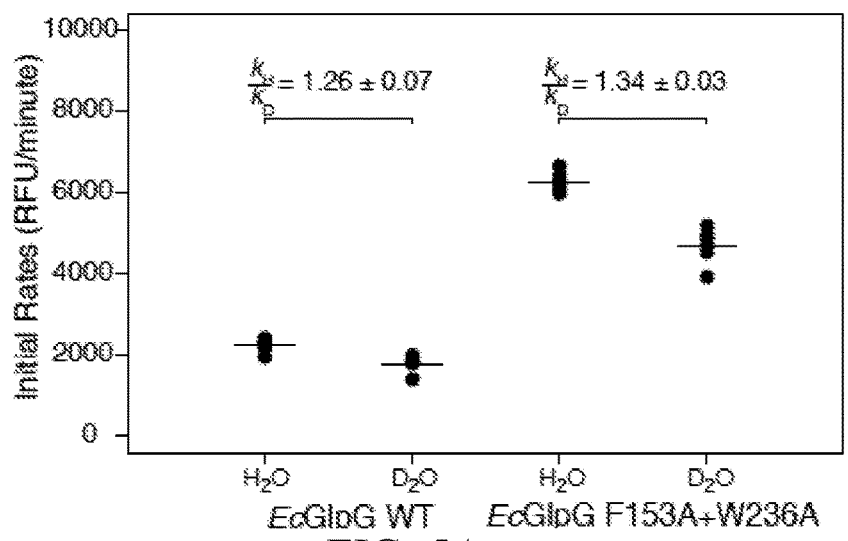
FIG. 5. Rate-limiting step for rhomboid proteolysis inside the membrane. (A) Rate analysis of FITC-TatA cleavage by EcGlpG in proteoliposomes in the presence of $H_2O$ versus $D_2O$. The weak (<<2) effect of $D_2O$ (expressed as a rates ratio) indicates hydrolysis is not rate limiting. (B) Titration analysis of FITC-TatA cleavage rate by EcGlpG in proteoliposomes in the presence of different proportions of $D_2O$. The linear effect indicates the slowing is due to perturbation of an equilibrium (exchange with protein groups), not a rate (hydrolysis step), effect. (C) Parallel real-time kinetic analysis of FITC-TatA cleavage by wildtype (filled circles) versus gate-open (F153A+W236A, open circles) EcGlpG in proteoliposomes was fit (left panel) with a Michaelis-Menten model (mean±sem, n=2, inset: fit±sd). Bar graph comparison (right panel) of the gate-open mutant effect on $k_{cat}$ (~3 fold faster) and $K_M$ (no change).
Figure 5B:
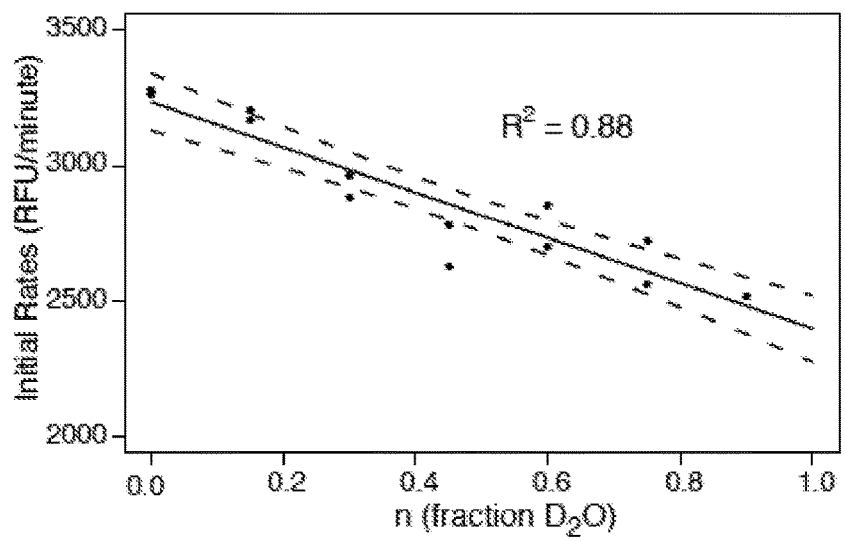

Interestingly however, $k_{cat}$ was ~6.5-fold faster in detergent than in proteoliposomes (FIG. 4A), revealing that the membrane environment slows proteolysis. It's generally accepted that hydrolysis within the membrane, where water is scarce, is rate-limiting for proteolysis. To test this directly, we performed a kinetic solvent isotope effect analysis by substituting deuterium oxide for water. A decrease in rate in deuterium oxide is commonly used to identify a rate-limiting hydrolysis step in a reaction (Fersht, 1999). Surprisingly, hydrolysis itself was not rate-limiting in membranes, since the ratio of the water/deuterium oxide proteolysis rates for GlpG was only a modest 1.26±0.32 (FIG. 5A) instead of the expected ≥2 for serine proteases (Elrod et al., 1980; Zhang and Kovach, 2006). In contrast, such mild effects are often caused by deuterium exchange with protein groups, and indeed we observed a gradual effect on proteolysis when we titrated deuterium oxide in the presence of water (FIG. 5B). This is diagnostic of an equilibrium effect on protein, rather than a direct effect on hydrolytic rate (Fersht, 1999).

Figure 5C:
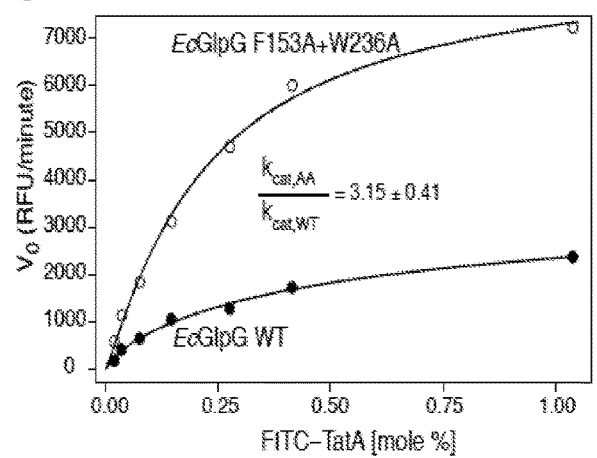
Figure 5C:
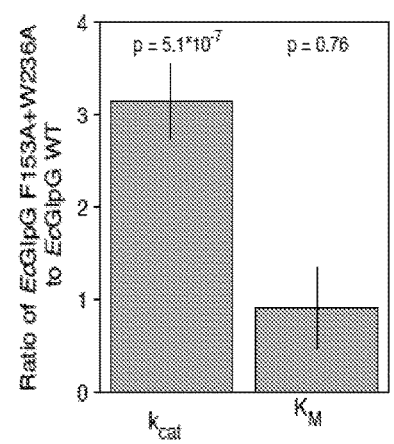

Conversely, we found that substrate gating plays a major role in determining reaction rate in the membrane (FIG. 5C). Analysis of gate-open relative to wildtype GlpG revealed a >3-fold increase in $k_{cat}$ without any change in $K_M$ (FIG. 5C) or cleavage site (FIG. 10), arguing that gate-opening is the rate-limiting step for proteolysis within the membrane. While recent structural studies with covalent inhibitors have suggested gating residues contribute to substrate binding (Xue and Ha, 2012), mutants in these residues do not change $K_M$. The membrane environment thus slows proteolytic rate, in part, by restraining protease gate opening, but $K_M$ appears to be inherently inefficient in all settings.

Kinetic Analysis of Diverse Rhomboid Proteases Reveals a Common Mechanism.

To our knowledge, it's unprecedented for the $K_M$ of a specific protease to play little or no role in driving proteolysis under physiological conditions (Perona and Craik, 1997; Timmer et al., 2009). To evaluate this possibility further, we characterized the effect of both protease and substrate variants.

Figure 6A:
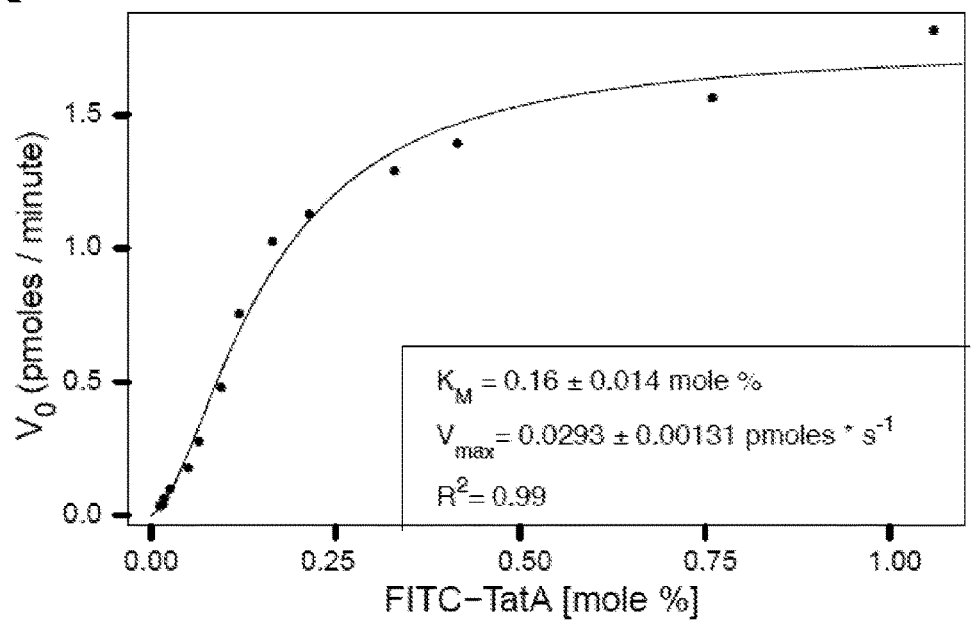
FIG. 6. Kinetics of membrane-immersed proteolysis by 9 diverse rhomboid proteases. (A) Michaelis-Menten model fit (inset: fit±sd) to real-time reaction velocity of FITC-TatA processing by HA-*Providencia stuartii* AarA (HA-PsAarA) in proteoliposomes. (B) Michaelis-Menten graphs of direct pairwise comparisons of eight diverse rhomboid proteases to HA-EcGlpG (HiGlpG: *Haemophilus influenzae* GlpG, PaROM: *Pseudomonas aeruginosa* ROM, VcRho: *Vibro cholerae* Rho, SpROM: *Streptococcus pneumoniae* ROM, AqROM: *Aquifex aeolicus* ROM, BfROM1/2: *Bacteroides fragilis*). See FIG. 10 for protein sequence alignment and accession numbers. (C) Comparison of kinetic parameters derived from Michaelis-Menten model fits (above: ratios±sd, below, p-values of pairwise model fitting with Bonferroni correction of $k_{cat}$ values). Patterned bars indicate AqROM analyzed at 85° C. and PaROM analyzed in liposomes composed of DMPC (asterisks denotes comparison to PaROM in *E. coli* liposomes). (D) A phylogenetic tree of analyzed rhomboid proteases and their best Michaelis-Menten parameters (fitted values±sd). Data is color-coded throughout the figure.
Figure 6B:
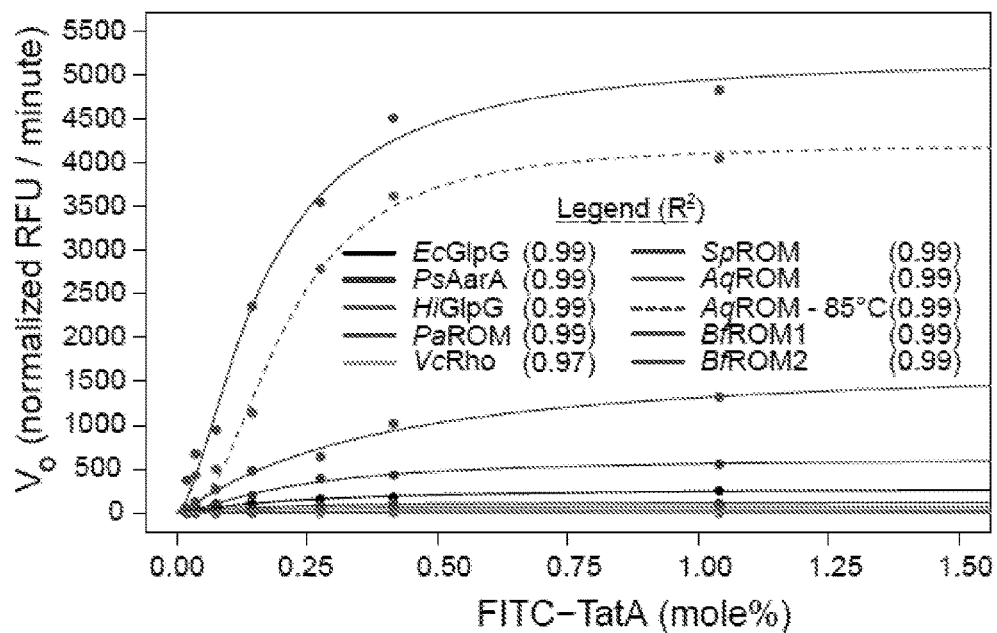
Figures 6C, 6D:
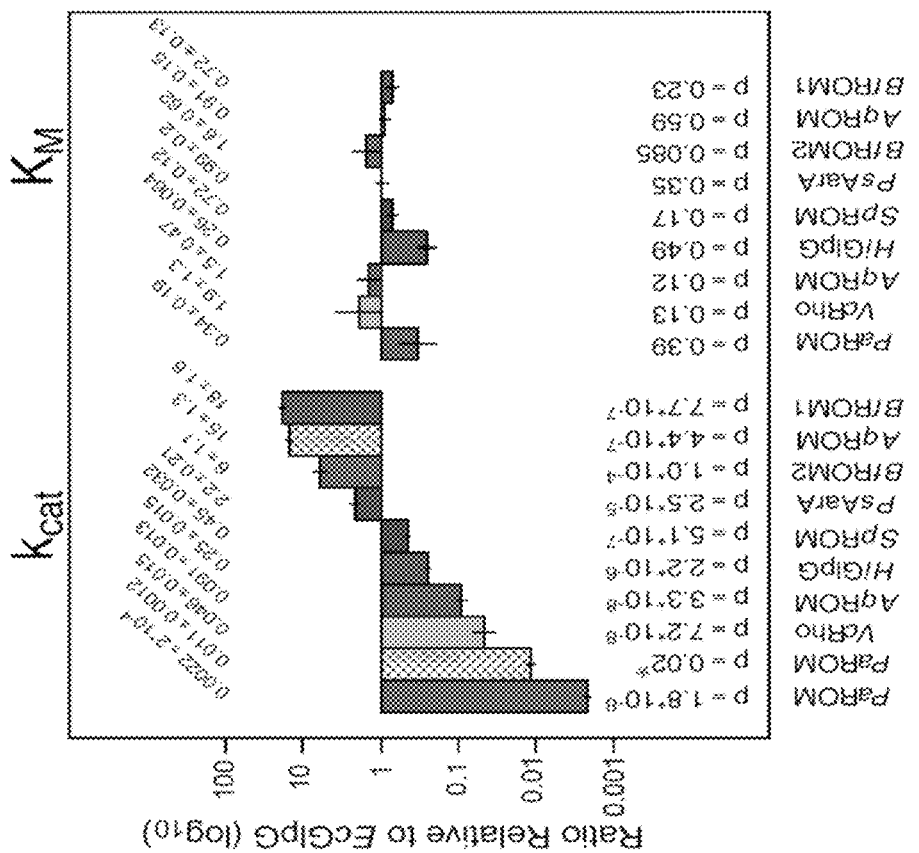
Figure 10:
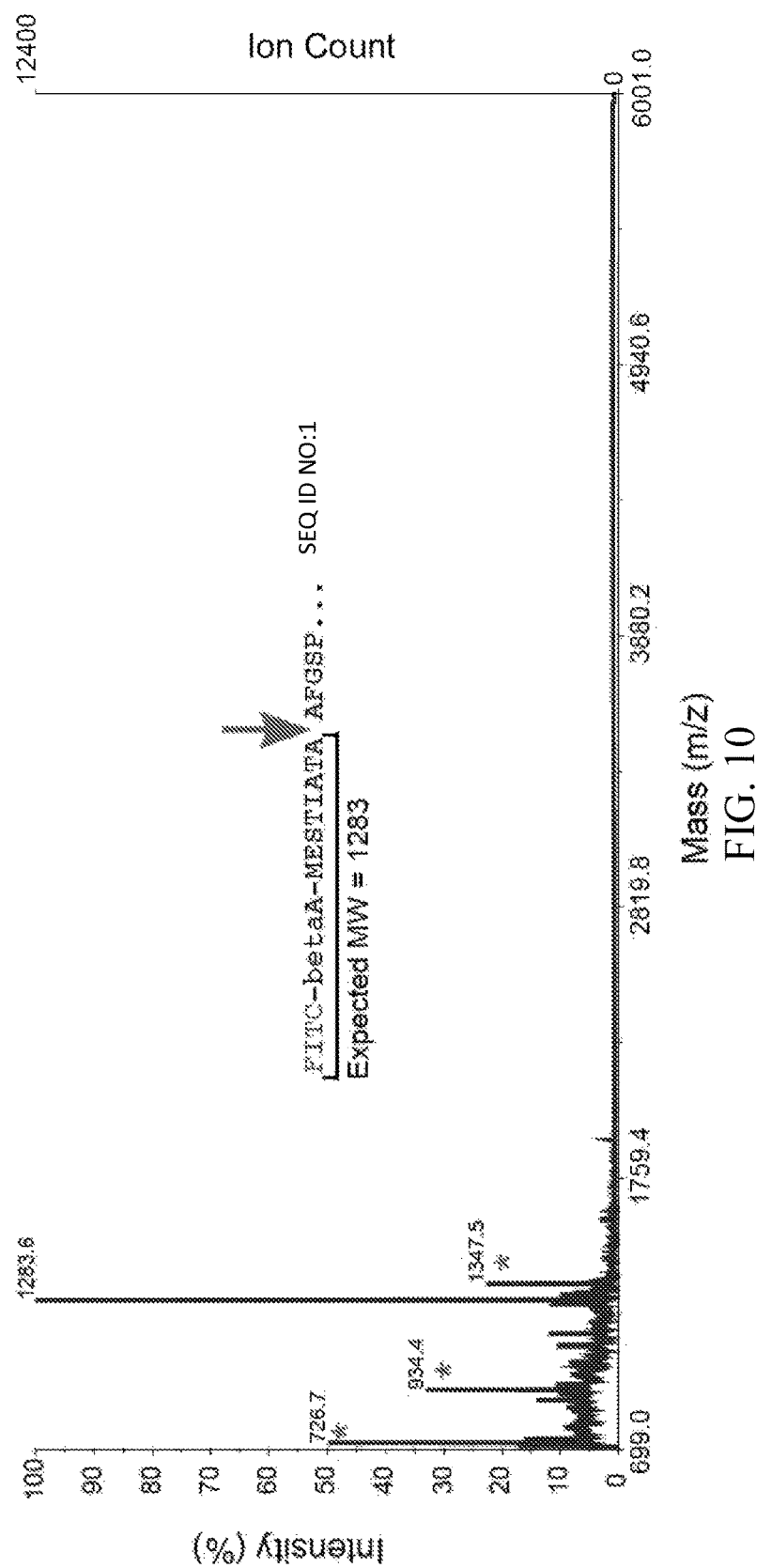
FIG. 10. MALDI/TOF mass spectral analysis of the FITC-TatA cleavage product produced by the gate-open mutant EcGlpG F153A+W236A. Red asterisks denote background peaks that correspond to no predicted mass/charge ratio of other potential cleavage sites. These are likely to be carryover lipid species.
Figure 11:
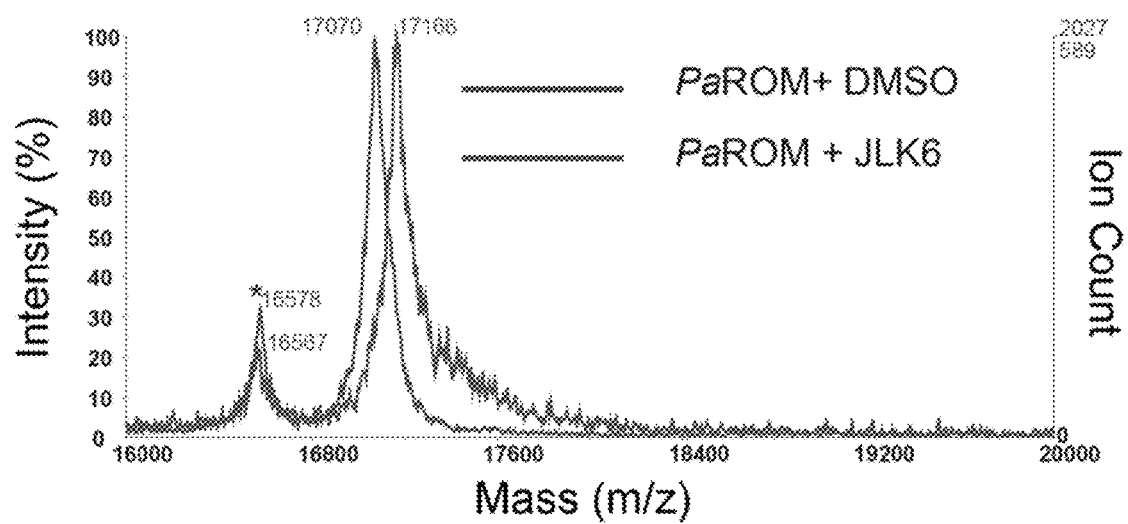
FIG. 11. Mass spectrum of PaROM, the slowest rhomboid analyzed, incubated with the activity-based inhibitor JLK6. Shown is the doubly-charged species. The asterisk denotes a background peak, which served as an internal control for the overlayed mass spectra. Data Not Shown: MUSCLE multiple sequence alignment of the 9 rhomboid proteases analyzed. Universally conserved residues are shaded in blue, and red stars denote active site serine and histidine residues. UNIPROT accession numbers are in parentheses.

Although *E. coli* GlpG is currently the best-characterized intramembrane protease, rhomboid proteases vary greatly in sequence (Lemberg and Freeman, 2007) and specific activity (Urban and Wolfe, 2005). We therefore measured the kinetic parameters for a panel of nine diverse rhomboid proteases that share <3% sequence identity (FIGS. 6A, 6B, and FIG. 10). Remarkably, despite varying ~10,000-fold in specific activity, all nine rhomboid proteases displayed indistinguishable $K_M$ values (FIG. 6C). In fact, even AarA, the natural protease that co-evolved with TatA (Stevenson et al., 2007), had, if anything, a slightly higher (less efficient) $K_M$ for TatA than GlpG (FIG. 6A-6D). Conversely, all differences in protease activity across this diverse panel of enzymes, when analyzed under identical conditions, were reflected in $k_{cat}$ changes alone, which ranged ~10,000-fold (FIGS. 6C and 6D).

Comparing a diverse set of rhomboid proteases to *E. coli* GlpG required maintaining equivalent conditions. As a result, a few rhomboid proteases were assayed under conditions that were physiological for *E. coli* GlpG, but different from what they would experience normally. Since these enzymes generally appeared less active than GlpG, we re-evaluated their activity under more physiological conditions. *Aquifex aeolicus* is an extreme thermophilic organism with a growth optimum of 85° C. (Deckert et al., 1998). Analysis of AqROM at 85° C. revealed a 250-fold increase in protease activity, all of which was reflected in a higher $k_{cat}$ with no corresponding decrease in $K_M$ (FIG. 6B-D). Similarly, although bacteria do not have phosphatidylcholine, the membranes of *Pseudomonas aeruginosa* accrue 4% phosphatidylcholine (and potentially other lipid species) as it assimilates choline during infection of its host (Wilderman et al., 2002). Analysis of PaROM revealed a >5-fold stimulation of its protease activity, but not that of other rhomboid proteases, by phosphatidylcholine, that again was accounted for by an increase in $k_{cat}$ (FIGS. 6C and D). Collectively, these observations strongly support the unexpected discovery that intramembrane proteolysis is fundamentally governed by $k_{cat}$, with little or no contribution from substrate-binding affinity.

Kinetic Analysis of Substrate Mutants Reveals No Binding Affinity Motif.

Figure 7A:
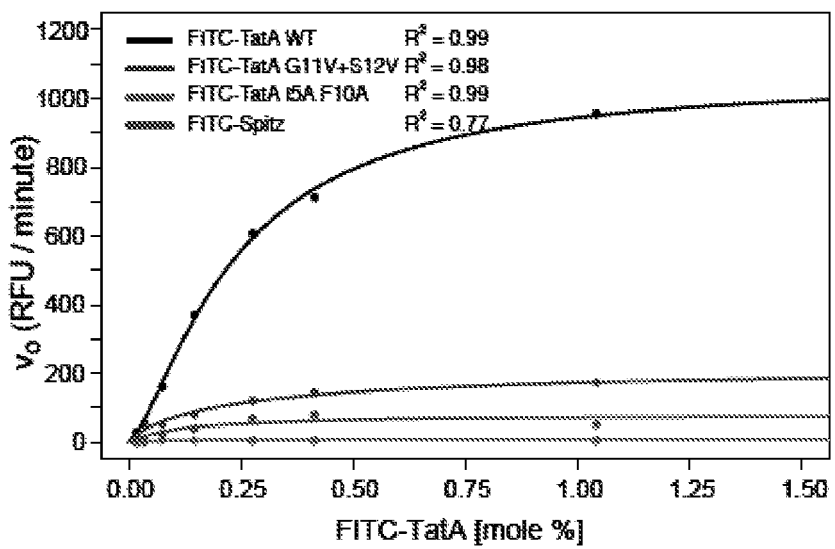
FIG. 7. Kinetic interpretation of defined intramembrane substrate variants. (A) Michael-Menten graphs of pairwise comparisons of FITC-TatA mutants and FITC-Spitz compared with FITC-TatA cleavage by HA-PsAarA. (B) Quantification of the kinetic parameters derived from the Michaelis-Menten model fits (above: ratios±sd, below, p-values of pairwise model fitting with Bonferroni correction of only $k_{cat}$ values). (C) Kinetic parameters for each substrate by HA-PsAarA (fitted values±sd). The 'recognition motif' is shaded in yellow, while the helix-destabilizing center is shaded in blue. (D) Model of rhomboid proteolysis inside the membrane compared to DNA glycosylase excision of damaged bases from duplex DNA. Substrates (damaged base for DNA glycosylase, transmembrane segment for rhomboid) are in red. White letters indicate the enzyme interrogation (I) and inner excision (E) sites. Kinetic parameters that we measured for *E. coli* GlpG are diagramed.
Figure 7B:
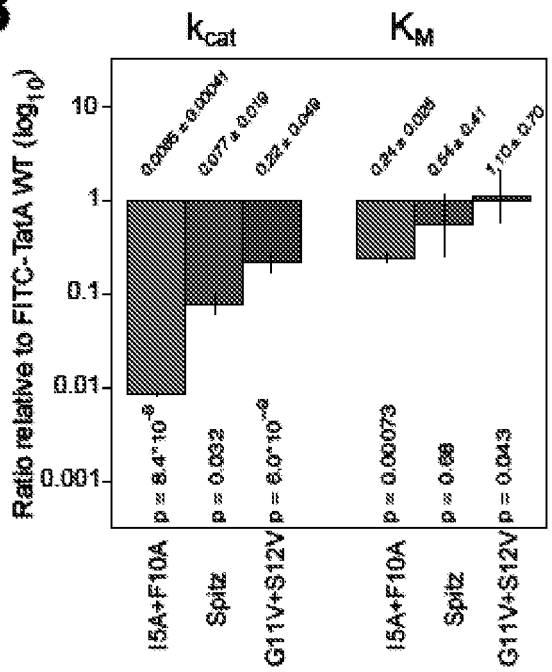
Figure 7C:
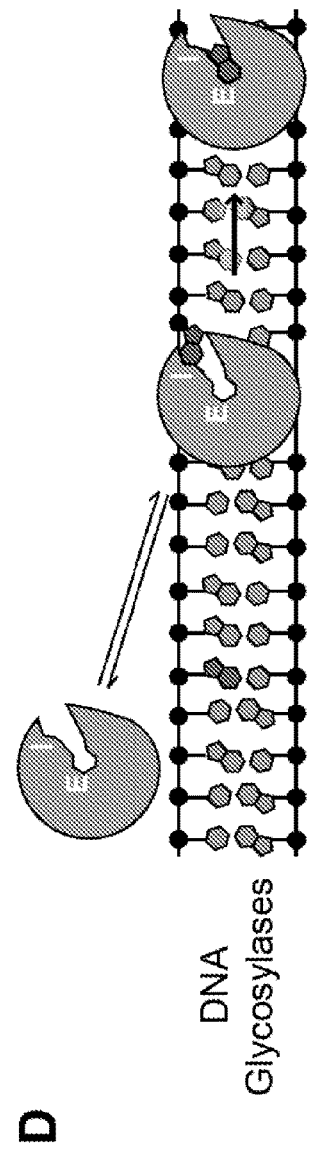

We also examined defined substrate mutants that have been under investigation for over a decade, but the lack of a kinetic system precluded rigorous mechanistic interpretation for how they affect proteolysis (reviewed in (Urban, 2010)). TatA itself has been subjected to extensive mutational analysis with >150 mutants, the outcome being interpreted as identification of a 'recognition motif' for sequence-specific binding comprised of large residues four residues preceding, and two residues following, the cleavage site (Strisovsky et al., 2009). We therefore examined a double mutant with disallowed alanines at these positions and indeed found proteolysis was decreased >100-fold (FIG. 7A). However, contrary to expectation for a sequence-binding motif, the mutant substrate actually decreased $K_M$ (p=0.00073), implying 4-fold improved binding (FIG. 7B). This result was also reassuring because it demonstrated that our assay was capable of measuring high affinity. The decrease in processing of the TatA double mutant was instead reflected in a >100-fold decrease in $k_{cat}$, which itself may account for the lower $K_M$ (FIGS. 7B and 7C). Overall, these findings are completely consistent with prior observations including mutagenesis data, but reveal that mutating apparent sequence motifs in substrates lowers proteolysis not by abrogating binding affinity ($K_M$ not increased), but by altering optimal exposure of the peptide bond for efficient hydrolysis (lowered $k_{cat}$).

Second, like all studied rhomboid substrates, TatA contains a region deeper within its transmembrane segment composed of helix-destabilizing residues that facilitate substrate unwinding prior to proteolysis (Moin and Urban, 2012a, b; Strisovsky et al., 2009). A mutant in these residues decreased TatA cleavage, but again reduced $k_{cat}$ without raising $K_M$ (FIGS. 7B and 7C). Lastly, the *Drosophila* signaling molecule Spitz, which is a less efficient substrate than TatA, also displayed lower $k_{cat}$ without any significant change in $K_M$ (FIGS. 7B and 7C). Together these defined substrate variants further indicate that intramembrane proteolysis is a kinetically controlled reaction that is not driven by affinity between protease and substrate.

To Develop and Pilot/Implement a Novel Membrane-Immersed Enzyme High-Throughput Screen for Rhomboid Protease Inhibitors.

The excellent behavior of this assay during our kinetic studies over the past year and as described in detail above suggests that high-throughput screening of catalysis directly inside the membrane environment is now feasible for the first time. We evaluated our assay in 384-well format with 3 different rhomboid enzymes, yielding Z'=0.80-0.92. We next screen-tested all 3 enzymes against a hand-assembled protease/membrane inhibitor library (>100 compounds), again yielding excellent consistency and evidence of inhibition by even weak serine protease inhibitors. Finally, we established conditions to ensure availability of all reagents for HTS, and now propose a series of defined steps with which to develop and optimize the assay for automated HTS and pilot screening.

Background.

Pathogens pose a constant and growing threat to human health, be it from acquired drug resistance by prevalent or emerging agents, or from weaponization of familiar microbes by bioterrorists. Slowed or neglected investment in developing antimicrobial agents has exacerbated this 'ticking time bomb' problem. Modern technological advances, especially the high-throughput screening (HTS) revolution, have made the path to compound discovery more systematic, promising both drug prototypes and research probes for gaining key insights into the molecular basis of disease.

Membranes are the first zones of combat between host and invading pathogens, making membrane-resident proteins central players in pathogenesis/defense. Over the past decade, proteases with active sites immersed inside the membrane have emerged at the core of circuits that regulate virulence in diverse pathogens. In protozoa like the malaria parasite, *Toxoplasma* and *Cryptosporidium* that are leading causes of death in AIDS patients, and dysenteric ameba, these parasite enzymes regulate adhesion with the host, and thus disease. Pathogenic bacteria, including *Mycobacterium tuberculosis, Vibrio cholerae*, and *Pseudomonas aeruginosa*, use intramembrane proteases as on/off switches for circuits that activate virulence or toxin production. These exciting advances have made this widespread class of microbial enzymes prime targets for combating disease.

Despite membrane proteins (e.g., GPCRs) and microbial proteases (e.g., HIV protease) being particularly effective drug targets historically, potent inhibitors have never been isolated for microbial intramembrane proteases. Crystal structures offer no reason for this discrepancy, because their active sites are exposed to the cell exterior. We recently discovered the membrane fundamentally alters their enzymatic properties, potentially explaining why inhibitors isolated with detergent-based systems prove largely ineffective in membrane settings. Unfortunately, these reactions have been inaccessible to direct screening in their natural membrane environment, until now. After a decade of effort, we overcome this challenge by developing, as described herein, an 'inducible' reconstitution system for the largest family of intramembrane proteases: rhomboid serine proteases. This system allows controlling and monitoring non-invasively and in real-time rhomboid catalysis immersed inside the membrane. Not only is this new assay already providing unexpected insights into how these novel enzymes function inside membranes, but we recently found it to be amenable to compound screening against these enzymes for the first time in their natural membrane setting.

Membrane-immersed protease reactions have been completely inaccessible to direct high-throughput screening in their native membrane environment until now. The few inhibitor development studies that have been attempted have all used rhomboid proteases suspended in detergent micelles and assayed with small quenched peptides that enter the active site from solution (rather than laterally via the membrane). Hits were rare, but even the small number that emerged all disappointingly failed to show even remotely similar potency when tested against rhomboid proteases in membranes relative to the detergent systems. As a consequence, the rhomboid protease field is still missing even a single potent or selective small molecule inhibitor, which remains the single biggest deficit facing this field.

Assay Evaluation.

We set up our assay in 384-well format, and sought to evaluate a Z' score for assay consistency. A significant advantage is that both substrate and enzyme are co-reconstituted into proteoliposomes as a master mix, such that there is minimal variation in substrate/enzyme addition per well. Since no potent rhomboid inhibitors are available, we set up reactions with wildtype versus the same levels of mutants in which we removed catalytic serine and histidine sidechains. All other parameters (e.g., FITC substrate, liposomes, buffer) remained exactly the same. Notably, even with manually hand-pipetted reactions and enzyme assay time of only 1 hour, the Z' factor of our assay was 0.80-0.92 (FIG. 12A). Although these values provided confidence for proceeding further with our preliminary studies, the excellent behavior observed with the current format suggests that we should be able to move to 1536-well format. Considering the increase in throughput, we next plan to explore the 1536 well option by optimizing substrate and enzyme concentration, lipid: protein ratios, and/or reaction times.

Assay Performance.

An important consideration is assay suitability for HTS, which we evaluated by manually screening a diverse panel of class-specific protease inhibitors (natural products, sulphonyl fluorides, hydroxamate-based metalloprotease inhibitors, vinyl sulfones, isocoumarins, chloromethyl ketones, proteasomal inhibitors, aspartyl protease inhibitors, cysteine protease inhibitors), a combinatorial library of peptide diphenyl-phosphonates, and over a dozen lipid enzyme inhibitors/drugs (some of which are known to affect other intramembrane proteases). We hand-assembled this library of 111 compounds because it represents likely candidates for real rhomboid inhibitors on the one hand, and on the other poses challenges for assay performance because most are chemically-reactive (warhead) molecules.

We performed this test independently again with three different rhomboid proteases, and even with hand-pipetted screens in 384-well format, in all three cases the assay performed very well (FIG. 12B). The variation was low over the 384-well plate, even with wells containing a potent protease inhibitor cocktail (Roche), which again emphasizes that rhomboid proteases are novel enzymes. Although no potent rhomboid inhibitors are currently available, an isocoumarin that is known to inhibit rhomboid activity at high concentrations yielded obvious evidence of inhibition of all three rhomboid proteases. Note that no compound pre-incubation with enzyme prior to the assay was performed, which is usually necessary for even detecting isocoumarin inhibition. Overall these are highly encouraging results that suggest this innovative assay is likely to be amenable to HTS for the discovery of novel rhomboid inhibitors.

DISCUSSION

In summary, we have developed an inducible reconstitution system for the analysis of intramembrane proteolysis in real time. This allowed us to measure for the first time the kinetic parameters of proteolysis occurring directly inside the membrane. Although the rhomboid domain is defined as a transmembrane segment binding moiety (Adrain and Freeman, 2012), all data with nine different rhomboid proteases and five substrate variants reveal protease and substrate have little, if any, meaningful affinity for each other within the membrane. This unexpected conclusion is independently supported by direct measurements of $K_d$ in the membrane using a new FRET-based assay, and in detergent micelles by a variety of approaches including equilibrium gel filtration. While our reconstitution system necessarily uses pure proteins to allow precise measurements, estimating 'apparent' kinetic parameters in living E. coli cells indicates that it faithfully recapitulates in vivo rhomboid properties. Lack of need for other cofactors is also consistent with divergent rhomboid enzymes rescuing mutant defects in radically different organisms (Gallio et al., 2002), and no additional components being uncovered in many saturation screens performed over the course of decades in both eukaryotes and prokaryotes (Casci and Freeman, 1999; Rather et al., 1999).

The central implication of the kinetic parameters is that proteolysis within the membrane is not driven by substrate affinity under physiological conditions. It's important to note that it's not the absolute $K_M$ value itself that leads to this conclusion: while some proteases like chymotrypsin also display high $K_M$ values (Wysocka et al., 2008), these digestive proteases encounter food protein at extraordinarily high and thus matched concentrations. Instead, although there is little precedent for interpreting binding affinities within 2-dimensions, a $K_M$ of ~0.14 mole percent is extraordinarily high, because the inner membrane of E. coli contains only 1.25-1.67 mole percent (~50% by weight) of total protein (Schnaitman, 1970a, b). Indeed, experimentally we found that substrate has to become nearly the most abundant protein in the E. coli membrane to be near $K_M$, and constitute all protein in a membrane to even approach $V_{max}$. Compared to other signaling proteases, rhomboid proteases are thus at least 2 to 3 orders of magnitude less efficient: the catalytic efficiency ($k_{cat}/K_M$) of E. coli GlpG, the best understood intramembrane protease, is only ~47 $M^{-1}s^{-1}$ (0.0063 $s^{-1}$/135 µM) relative to >10,000 $M^{-1}s^{-1}$ for caspases (Stennicke et al., 2000; Timmer et al., 2009).

Instead, these properties force us to consider that membrane-immersed proteolysis may be organized differently from other forms of proteolysis. All changes we observed involve $k_{cat}$, revealing intramembrane proteolysis is fundamentally a kinetically-controlled reaction, rather than relying on differences in protein affinity (i.e. not thermodynamically-controlled). Interestingly, these enzymatic properties are unlike those of any other proteases or membrane proteins studied, but strikingly parallel those of one subset of DNA repair enzymes.

Figure 7D:

DNA glycosylases remove damaged bases from DNA using an intriguing mechanism that involves two different enzyme sites (FIG. 7D). Nucleotides flipped out of a DNA double helix first interact with an 'interrogation site' on the DNA glycosylase (Friedman and Stivers, 2010) Importantly, a damaged base is not bound with high affinity per se; instead, it is able to spend more time in the dynamic, extrahelical state and thus stay longer in the interrogation complex. This longer residence allows the base to translocate to a second, deeper site—the excision site—where the glycosidic linkage is clipped to excise the base from DNA. The discriminatory mechanism is therefore rate-governed, with a minor contribution from binding affinity to the damaged base itself. The second key property of these DNA glycosylases is a slow $k_{cat}$, because it ensures catalysis is slower than the residence time of natural bases, kinetically protecting them from hydrolysis (Friedman and Stivers, 2010).

These striking parallels suggest that low substrate affinity and slow rate of rhomboid proteolysis are not defects, but rather features, of this enzyme system. Moreover, they offer a new mechanistic framework for interpreting how membrane-immersed proteolysis is organized (FIG. 7D). First, the lack of affinity for substrates and reliance on rates suggests that rhomboid proteases may also use an analogous 'interrogation' site to discriminate substrate from non-substrate kinetically. Although the gate has been viewed simply as a point of substrate entry, the crevice created by gate-opening, which is stable in the membrane (Urban and Baker, 2008; Zhou et al., 2012), may actually be an 'interrogation' site (FIG. 7D). Like with DNA glycosylases, this site is physically separated from the deeper active site, which would force transmembrane helices to reside in the unwound state to reach the catalytic residues for proteolysis to ensue (FIG. 7D), instead of returning laterally to the membrane. Our recent spectroscopy analysis of substrates revealed they form inherently less stable helices than non-substrates (Moin and Urban, 2012a), which suggests that they would spend more time in the unfolded state and thus reach the inner active site from the interrogation site.

This model may also explain the infamous property that rhomboid proteases use a catalytically weak dyad instead of evolving a classical triad to enhance catalytic power. While dyads are rare among serine proteases, the reduced catalytic rate would help protect non-substrates kinetically from cleavage by ensuring sufficient time for them to escape back into the membrane before cleavage could occur. In fact, the slow $k_{cat}$ of 0.02 s$^-$ that we measured for gate-open GlpG is much like the $k_{cat}$ of 0.03 s$^{-1}$ exhibited by human DNA glycosylase OGG1 (Kuznetsov et al., 2007).

It is thus tempting to speculate that the primordial function of rhomboid proteases was to patrol the membrane looking for unfolded membrane proteins to cleave as a repair mechanism analogous to how DNA glycosylases patrol the genome for damaged bases. Nevertheless, since comparing intramembrane proteases to DNA repair enzymes is entirely new, it requires focused testing to determine to what degree rhomboid function is like that of DNA glycosylases, and where it deviates. Our discovery also has practical implications for inhibitor design; since substrate affinity is low, commonly-used strategies that rely on substrate characteristics to target inhibitor warheads to proteases (Drag and Salvesen, 2010) are unlikely to produce potent compounds against rhomboid. Likewise, caution should be exercised when interpreting covalent inhibitor-bound GlpG structures in what they can teach us about natural substrate binding (Vinothkumar et al., 2010; Xue et al., 2012). On an optimistic note, a robust kinetic system will allow evaluating inhibitors based on precise $K_i$ values and directly within membranes, instead of relying on $IC_{50}$ concentrations that are condition-dependent.

We focused our analyses on rhomboid proteases, but it should be noted that such quantitative real-time analyses have yet to be realized with other intramembrane proteases. In fact, a major achievement is the recent application of kinetic analysis to γ-secretase (Chavez-Gutierrez et al., 2012), albeit in detergent extracts and with endpoint assays. In this light, a particularly exciting feature of our system is its potential to be applied broadly: all protease catalysis is pH-sensitive, and similar placement of a FITC label should also afford natural quenching of other substrates upon membrane reconstitution. Alternatively, γ-secretase and site-2 proteases could be switched on after reconstitution by washing out reversible inhibitors, or supplying zinc ions, respectively. It is possible that some intramembrane proteases like γ-secretase could exhibit different kinetics, since they evolved extramembraneous domains for substrate binding (Fleig et al., 2012; Li et al., 2009; Shah et al., 2005). However, since these are later adaptations, low intramembrane affinity may be a primordial and common property of intramembrane proteolysis. Whether weak binding at transmembrane sites is important for catalysis inside the membrane, or a deliberate specialization by this class of enzymes, remains to be determined.

Supplemental Materials and Methods

DNA Cloning.

Rhomboid proteases were cloned by PCR amplification from purified genomic DNA (ATCC) with primers encoding a single N-terminal HA-tag. All constructs were verified by sequencing the entire ORF.

Thermostability Analysis.

HA-EcGlpG was preincubated at pH 4 with 10 mM NaAcetate, 150 mM NaCl, 0.1% DDM or pH 7 with 50 mM Tris pH 7.4, 150 mM NaCl, 0.1% DDM for 1 hour at room temperature, after which the proteins were neutralized with 7 volumes of 50 mM Tris pH 7.4, 150 mM NaCl, 0.1% DDM. Thermostability was assayed as previously described (Baker and Urban, 2012) using a Stargazer-384 instrument (Harbinger Biotech).

Rhomboid Protease Crystallization and Structure Determination.

DN-GlpG from *E. coli* was expressed and purified as described previously (Wu et al., 2006), and crystallized in hanging drops at pH 4.5 in 0.1M Na-Acetate, 3M NaCl and 10% glycerol and at pH 7.5 in 0.1M HEPES, 3M NaCl and 10% Glycerol at room temperature. Crystals were cryo-protected in a reservoir buffer containing 15% (v/v) Glycerol and flash-frozen in a nitrogen stream. X-ray diffraction data were collected at F1 station of the Cornell High Energy Synchrotron Source (CHESS), and processed using HKL2000 (Otwinowski and Minor, 1997). The structures were solved by molecular replacement using the coordinate of native GlpG (PDB entry 2IC8) as the probe with the program MOLREP in the CCP4 program suite (1994). Initial refinement was performed using CNS (Brunger et al., 1998) with positional, simulated annealing, and individual temperature factor refinement protocols. Model building was carried out iteratively in coot (Emsley and Cowtan, 2004) based on $\sigma_A$-weighted $2F_o$-$F_c$ and $F_o$-$F_c$ maps. After CNS refinement converged, further refinement was conducted with REFMAC5 (Murshudov et al., 2011). The final model for both GlpG structures contained residues 91-272.

CysTatA-His Cleavage Assay.

CysTatA-His (expressed from pET27b as residues 1-33 of 97 with a C-terminal poly6-His fusion and a cysteine inserted after the start codon) was purified using a $Ni^{2+}$ affinity resin (Roche), concentrated to ~500 μM and dialyzed against 50 mM Tris, 150 mM NaCl, 0.2% sarkosyl, and 1 mM DTT. Purified CysTatA-His was reconstituted as described into *E. coli* lipids with either HA-EcGlpG WT or the catalytic mutant HA-EcGlpG S201A+H254A. Reactions were incubated at 37° C. and time points of each reaction were quenched with SDS-sample buffer. Samples were resolved on a 16% polyacrylamide, 6 M urea, SDS, tricine gel at 120 V for 2 hours. After transfer to a nitrocellulose membrane, the membrane was probed with a mouse anti-His-647 direct conjugated antibody (Qiagen) and imaged with an Odyssey infrared scanner.

Mass Spectrometry of FITC-TatA Cleavage.

FITC-TatA cleaved in proteoliposomes was filtered through a 30,000 MW cutoff centrifugal filter (Millipore) following the manufacturers protocol. The sample was purified using a C18 ZipTip (Millipore), and analyzed by MALDI-TOF using a Voyager DE-STR mass spectrometer calibrated with bradykinin fragment 1-7, angiotensin I, ACTH fragment 18-39, and insulin oxidized B chain (Sigma-Aldrich).

FITC-TatA Labeling and Orientation.

400 pmoles of FITC-TatA, containing a single cysteine at the C-terminus, was reconstituted into *E. coli* lipids to 0.5 mole %. Following ultracentrifugation, membrane pellets were resuspended with 50 mM Tris pH 7.4, 150 mM NaCl with or without 0.2% sarkosyl. DMSO or 4 μmoles of the membrane-impermeable IR800cw-maleimide dye (LiCor Biosciences) was added to each sample as indicated and incubated at room temperature for 2 hours to label exposed cysteines. Labeling was quenched by adding 1,000 μmoles of DTT and incubating for 30 minutes. Samples were resolved by SDS-PAGE and imaged with an Odyssey infrared scanner (LiCor Biosciences) in both the 700 and 800 channels.

Active Site Labeling.

Purified rhomboid proteases were labeled with the activity-based isocoumarin inhibitor JLK6 (Tocris Biosciences) to determine the fraction of purified protein that was active. Rhomboid protein in 50 mM Tris pH 7.4, 150 mM NaCl, 0.1% DDM was incubated with either 10% DMSO only or carrying 400 mM JLK6 at 37° C. for 3 hours, purified using a C4 ZipTip, and analyzed by mass spectrometry as described previously (Pierrat et al., 2011).

FRET Analysis of Protease-Substrate Affinity in Membranes.

Purified N-terminally His-tagged EcGlpG H254A+C104A+W196C protein was labeled at the single cysteine residue with the FRET acceptor tetramethylrhodamine-5-maleimide (TMR) (Life Technologies). Reconstitutions into *E. coli* liposomes were performed as described above, except that 30 pmoles of TMR-labeled protein was mixed with 25-800 pmoles of the FITC-TatA ligand. Following reconstitution, the samples were incubated at 37° C. in a Synergy H4 Hybrid plate reader. Fluorescence was measured with excitation at 485 nm and emission from 510-600 nm in 5 nm intervals. The FRET interaction was calculated at the 580 nm emission wavelength by subtracting the TMR-labeled GlpG protein alone and the FITC-TatA alone samples from the sample containing both macromolecules.

Proteolysis Assays in Detergent Micelles.

Cleavage reactions of APP+Spi7-Flag were performed as described previously and imaged with an Odyssey infrared scanner (LiCor Biosciences) (Baker and Urban, 2012; Baker et al., 2007). The kinetics of FITC-TatA cleavage were examined under different conditions and in various detergents before settling on the following optimized protocol: FITC-TatA in 50 mM Tris pH 7.4, 150 mM NaCl, 1 mM DTT, 0.15% Sarkosyl, 0.1% (w/v) DDM was pre-incubated at 37° C. for 10 minutes, centrifuged at 13,000 rpm in a microcentrifuge for 10 minutes to remove any insoluble substrate, and mixed with 83 nM HA-EcGlpG in reaction tubes pre-warmed to 37° C. Reactions were quenched and analyzed on 16% tricine gels as above. Actual substrate concentrations were calibrated using FITC-TatA standards analyzed in parallel.

Co-Precipitation Analysis.

2.5 μM His-tagged EcGlpG C104A+H254A with 70 μM FITC-TatA was incubated with pre-equilibrated $Ni^{2+}$-NTA resin (Qiagen) for 3 hours at room temperature. The resin was washed, and bound proteins were eluted with SDS-sample buffer for 30 minutes. FITC-TatA was detected as above using a 16% Tricine gel and a Typhoon Imager. His-EcGlpG C104A+H254A was detected by western blot with the mouse anti-penta-His antibody (Qiagen), and imaged with an Odyssey infrared scanner (LiCor Biosciences).

HPLC Equilibrium Gel Filtration Analysis.

Two Superdex 200 PC 3.2/30 high-resolution gel filtration columns (GE Healthcare) were connected in tandem to a ProStar 410 HPLC system (Agilent/Varian), and equilibrated with 9.5 μM FITC-TatA in 2 mM phosphate buffer pH 7.4, 25 mM Tris pH 7.4, 120 mM NaCl, 0.15% Sarkosyl, 0.1% DDM, 1 mM DTT. 20 μM HA-EcGlpG S201A+H254A was preincubated with 9.5 μM FITC-TatA, and 50 μL was injected using an Autosampler 410 onto the columns at a flow rate of 0.05 mL/minute. Elution was monitored by absorbance at all wavelengths between 200 to 600 nm simultaneously using a PDA 330 detector. The FITC-TatA peak was quantified relative to known FITC-TatA concentration standards that were run on the columns equilibrated with 9.5 μM FITC alone in buffer. Conventional gel filtration was conducted under similar conditions, except the columns were equilibrated with buffer lacking FITC-TatA.

Chromosomal Engineering of *E. coli*.

Allelic exchange 'knock-in' of the *E. coli* chromosomal glpG gene was achieved by two successive rounds of homologous recombination using standard recombineering methods (Datsenko and Wanner, 2000). In the first round, the entire glpG gene was replaced in BW25113 $Str^R$ cells via homologous flanking ends with a cassette that encodes a selection and a counter-selection marker (cat-rpsL: chloramphenicol acetyltransferase [cat] and wild-type rpsL to confer resistance to chloramphenicol and sensitivity to streptomycin, respectively) by selecting for growth in the presence of 17.5 μg/mL chloramphenicol. In the second round, the now chromosomally encoded cassette was replaced with either a Flag or hemagglutinin epitope tag fused to the 5' end of the glpG DNA sequence (Flag-GlpG or HA-GlpG) using the same flanking homology ends by counter-selecting for the desired strain for growth in the presence of 200 µg/mL streptomycin. The resulting strains, Flag-GlpG and HA-GlpG, were confirmed by PCR and sequencing.

REFERENCES

1. Adrain, C., and Freeman, M. (2012). New lives for old: evolution of pseudoenzyme function illustrated by iRhoms. Nature reviews Molecular cell biology 13, 489-498.
2. Baker, R. P., and Urban, S. (2012). Architectural and thermodynamic principles underlying intramembrane protease function. Nature chemical biology 8, 759-768.
3. Baker, R. P., Young, K., Feng, L., Shi, Y., and Urban, S. (2007). Enzymatic analysis of a rhomboid intramembrane protease implicates transmembrane helix 5 as the lateral substrate gate. Proc Natl Acad Sci USA 104, 8257-8262.
4. Casci, T., and Freeman, M. (1999). Control of EGF receptor signalling: Lessons from fruitflies. Cancer and Metastasis Rev 18, 181-201.
5. Chavez-Gutierrez, L., Bammens, L., Benilova, I., Vandersteen, A., Benurwar, M., Borgers, M., Lismont, S., Zhou, L., Van Cleynenbreugel, S., Esselmann, H., et al. (2012). The mechanism of gamma-Secretase dysfunction in familial Alzheimer disease. EMBO J 31, 2261-2274.
6. De Strooper, B., and Annaert, W. (2010). Novel research horizons for presenilins and gamma-secretases in cell biology and disease. Annu Rev Cell Dev Biol 26, 235-260.
7. Deckert, G., Warren, P. V., Gaasterland, T., Young, W. G., Lenox, A. L., Graham, D. E., Overbeek, R., Snead, M. A., Keller, M., Aujay, M., et al. (1998). The complete genome of the hyperthermophilic bacterium *Aquifex aeolicus*. Nature 392, 353-358.
8. Doucet, A., Butler, G. S., Rodriguez, D., Prudova, A., and Overall, C. M. (2008). Metadegradomics: toward in vivo quantitative degradomics of proteolytic post-translational modifications of the cancer proteome. Mol Cell Proteomics 7, 1925-1951.
9. Drag, M., and Salvesen, G. S. (2010). Emerging principles in protease-based drug discovery. Nature reviews 9, 690-701.
10. Elrod, J. P., Hogg, J. L., Quinn, D. M., Venkatasubban, K. S., and Schowen, R. L. (1980). Protonic Reorganization and Substrate Structure in Catalysis by Serine Proteases. J Am Chem Soc 102, 3917-3922.
11. Fersht, A. (1999). Structure and Mechanism in Protein Science: A Guide to Enzyme Catalysis and Protein Folding (New York: W. H. Freeman and Company).
12. Fleig, L., Bergbold, N., Sahasrabudhe, P., Geiger, B., Kaltak, L., and Lemberg, M. K. (2012). Ubiquitin-Dependent Intramembrane Rhomboid Protease Promotes ERAD of Membrane Proteins. Mol Cell 47, 558-569.
13. Fluhrer, R., Steiner, H., and Haass, C. (2009). Intramembrane proteolysis by signal peptide peptidases: a comparative discussion of GXGD-type aspartyl proteases. J Biol Chem 284, 13975-13979.
14. Friedman, J. I., and Stivers, J. T. (2010). Detection of damaged DNA bases by DNA glycosylase enzymes. Biochemistry (Mosc) 49, 4957-4967.
15. Gallio, M., Sturgill, G., Rather, P., and Kylsten, P. (2002). A conserved mechanism for extracellular signaling in eukaryotes and prokaryotes. Proc Natl Acad Sci USA 99, 12208-12213.
16. Hummel, J. P., and Dreyer, W. J. (1962). Measurement of protein-binding phenomena by gel filtration. Biochim Biophys Acta 63, 530-532.
17. Huntington, J. A. (2012). Thrombin plasticity. Biochim Biophys Acta 1824, 246-252.
18. Kuznetsov, N. A., Koval, V. V., Nevinsky, G. A., Douglas, K. T., Zharkov, D. O., and Fedorova, O. S. (2007). Kinetic conformational analysis of human 8-oxoguanine-DNA glycosylase. J Biol Chem 282, 1029-1038.
19. Lazareno-Saez, C., Arutyunova, E., Coquelle, N., and Lemieux, M. J. (2013). Domain swapping in the cytoplasmic domain of the *Escherichia coli* rhomboid protease. J Mol Biol 425, 1127-1142.
20. Lemberg, M. K., and Freeman, M. (2007). Functional and evolutionary implications of enhanced genomic analysis of rhomboid intramembrane proteases. Genome Res 17, 1634-1646.
21. Li, X., Dang, S., Yan, C., Gong, X., Wang, J., and Shi, Y. (2013). Structure of a presenilin family intramembrane aspartate protease. Nature 493, 56-61.
22. Li, X., Wang, B., Feng, L., Kang, H., Qi, Y., Wang, J., and Shi, Y. (2009). Cleavage of RseA by RseP requires a carboxyl-terminal hydrophobic amino acid following DegS cleavage. Proc Natl Acad Sci USA 106, 14837-14842.
23. Lopez-Otin, C., and Bond, J. S. (2008). Proteases: multifunctional enzymes in life and disease. J Biol Chem 283, 30433-30437.
24. Makinoshima, H., and Glickman, M. S. (2006). Site-2 proteases in prokaryotes: regulated intramembrane proteolysis expands to microbial pathogenesis. Microbes Infect 8, 1882-1888.
25. Moin, S. M., and Urban, S. (2012a). Membrane immersion allows rhomboid proteases to achieve specificity by reading transmembrane segment dynamics. eLife 1, e00173.
26. Osenkowski, P., Ye, W., Wang, R., Wolfe, M. S., and Selkoe, D. J. (2008). Direct and potent regulation of gamma-secretase by its lipid microenvironment. J Biol Chem 283, 22529-22540.
27. Perona, J. J., and Craik, C. S. (1997). Evolutionary divergence of substrate specificity within the chymotrypsin-like serine protease fold. J Biol Chem 272, 29987-29990.
28. Rather, P. N., Ding, X., Baca-DeLancey, R. R., and Siddiqui, S. (1999). *Providencia stuartii* genes activated by cell-to-cell signaling and identification of a gene required for production or activity of an extracellular factor. J Bacteriol 181, 7185-7191.
29. Schnaitman, C. A. (1970a). Examination of the protein composition of the cell envelope of *Escherichia coli* by polyacrylamide gel electrophoresis. J Bacteriol 104, 882-889.
30. Schnaitman, C. A. (1970b). Protein composition of the cell wall and cytoplasmic membrane of *Escherichia coli*. J Bacteriol 104, 890-901.
31. Shah, S., Lee, S. F., Tabuchi, K., Hao, Y. H., Yu, C., LaPlant, Q., Ball, H., Dann, C. E., 3rd, Sudhof, T., and Yu, G. (2005). Nicastrin functions as a gamma-secretase-substrate receptor. Cell 122, 435-447.
32. Stennicke, H. R., Renatus, M., Meldal, M., and Salvesen, G. S. (2000). Internally quenched fluorescent peptide substrates disclose the subsite preferences of human caspases 1, 3, 6, 7 and 8. Biochem J 350 Pt 2, 563-568.
33. Stevenson, L. G., Strisovsky, K., Clemmer, K. M., Bhatt, S., Freeman, M., and Rather, P. N. (2007). Rhomboid protease AarA mediates quorum-sensing in *Providencia stuartii* by activating TatA of the twin-arginine translocase. Proc Natl Acad Sci USA 104, 1003-1008.

34. Strisovsky, K., Sharpe, H. J., and Freeman, M. (2009). Sequence-specific intramembrane proteolysis: identification of a recognition motif in rhomboid substrates. Mol Cell 36, 1048-1059.
35. Timmer, J. C., Zhu, W., Pop, C., Regan, T., Snipas, S. J., Eroshkin, A. M., Riedl, S. J., and Salvesen, G. S. (2009). Structural and kinetic determinants of protease substrates. Nature structural & molecular biology 16, 1101-1108.
36. Urban, S. (2009). Making the cut: central roles of intramembrane proteolysis in pathogenic microorganisms. Nature Reviews Microbiology 7, 411-423.
37. Urban, S. (2010). Taking the plunge: integrating structural, enzymatic and computational insights into a unified model for membrane-immersed rhomboid proteolysis. Biochem J 425, 501-512.
38. Urban, S., and Baker, R. P. (2008). In vivo analysis reveals substrate-gating mutants of a rhomboid intramembrane protease display increased activity in living cells. Biol Chem 389, 1107-1115.
39. Urban, S., and Dickey, S. W. (2011). The rhomboid protease family: a decade of progress on function and mechanism. Genome biology 12, 231.
40. Urban, S., and Wolfe, M. S. (2005). Reconstitution of intramembrane proteolysis in vitro reveals that pure rhomboid is sufficient for catalysis and specificity. Proc Natl Acad Sci USA 102, 1883-1888.
41. Vinothkumar, K. R., Strisovsky, K., Andreeva, A., Christova, Y., Verhelst, S., and Freeman, M. (2010). The structural basis for catalysis and substrate specificity of a rhomboid protease. EMBO J 29, 3797-3809.
42. Wilderman, P. J., Vasil, A. I., Martin, W. E., Murphy, R. C., and Vasil, M. L. (2002). *Pseudomonas aeruginosa* synthesizes phosphatidylcholine by use of the phosphatidylcholine synthase pathway. J Bacteriol 184, 4792-4799.
43. Wolfe, M. S. (2009). Intramembrane proteolysis. Chem Rev 109, 1599-1612.
44. Wysocka, M., Lesner, A., Legowska, A., Jaskiewicz, A., Miecznikowska, H., and Rolka, K. (2008). Designing of substrates and inhibitors of bovine alpha-chymotrypsin with synthetic phenylalanine analogues in position P(1). Protein and peptide letters 15, 260-264.
45. Xue, Y., Chowdhury, S., Liu, X., Akiyama, Y., Ellman, J., and Ha, Y. (2012). Conformational change in rhomboid protease GlpG induced by inhibitor binding to its S' subsites. Biochemistry (Mosc) 51, 3723-3731.
46. Xue, Y., and Ha, Y. (2012). Catalytic mechanism of rhomboid protease GlpG probed by 3,4-dichloroisocoumarin and diisopropyl fluorophosphonate. J Biol Chem 287, 3099-3107.
47. Zhang, D., and Kovach, I. M. (2006). Deuterium solvent isotope effect and proton-inventory studies of factor Xa-catalyzed reactions. Biochemistry (Mosc) 45, 14175-14182.
48. Zhou, Y., Moin, S. M., Urban, S., and Zhang, Y. (2012). An internal water-retention site in the rhomboid intramembrane protease GlpG ensures catalytic efficiency. Structure 20, 1255-1263.
49. (1994). The CCP4 suite: programs for protein crystallography. Acta Crystallogr D *Biol Crystallogr* 50, 760-763.
50. Baker, R. P., and Urban, S. (2012). Architectural and thermodynamic principles underlying intramembrane protease function. Nature chemical biology 8, 759-768.
51. Baker, R. P., Young, K., Feng, L., Shi, Y., and Urban, S. (2007). Enzymatic analysis of a rhomboid intramembrane protease implicates transmembrane helix 5 as the lateral substrate gate. Proc Natl Acad Sci USA 104, 8257-8262.
52. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., et al. (1998). Crystallography & NMR system: A new software suite for macromolecular structure determination. Acta Crystallogr D Biol Crystallogr 54, 905-921.
53. Datsenko, K. A., and Wanner, B. L. (2000). One-step inactivation of chromosomal genes in *Escherichia coli* K-12 using PCR products. Proc Natl Acad Sci USA 97, 6640-6645.
54. Emsley, P., and Cowtan, K. (2004). Coot: model-building tools for molecular graphics. Acta Crystallogr D Biol Crystallogr 60, 2126-2132.
55. Murshudov, G. N., Skubak, P., Lebedev, A. A., Pannu, N. S., Steiner, R. A., Nicholls, R. A., Winn, M. D., Long, F., and Vagin, A. A. (2011). REFMAC5 for the refinement of macromolecular crystal structures. Acta Crystallogr D Biol Crystallogr 67, 355-367.
56. Otwinowski, Z., and Minor, W. (1997). Processing of X-ray diffraction data collected in oscillation mode. Methods Enzymol 276, 307-326.
57. Pierrat, O. A., Strisovsky, K., Christova, Y., Large, J., Ansell, K., Bouloc, N., Smiljanic, E., and Freeman, M. (2011). Monocyclic beta-lactams are selective, mechanism-based inhibitors of rhomboid intramembrane proteases. ACS chemical biology 6, 325-335.
58. Wu, Z., Yan, N., Feng, L., Oberstein, A., Yan, H., Baker, R. P., Gu, L., Jeffrey, P. D., Urban, S., and Shi, Y. (2006). Structural analysis of a rhomboid family intramembrane protease reveals a gating mechanism for substrate entry. Nature structural & molecular biology 13, 1084-1091.

We claim:

1. A method of screening for modulators of an intramembrane protease comprising the steps of:
   a. contacting in a mixture the protease and a substrate with a lipid under acidic or basic conditions to (i) form a membrane comprising the lipid bilayer, protease and the substrate and (ii) render the protease catalytically inactive;
   b. contacting a test agent with the membrane mixture;
   c. adjusting the pH to physiological conditions to render the protease catalytically active;
   d. assaying substrate cleavage by the protease; and
   e. comparing the assayed substrate cleavage to a reference that does not include the test agent, wherein an increase or a decrease of substrate cleavage by the protease relative to the reference identifies the test agent as a modulator of the intramembrane protease.

2. The method of claim 1, wherein the intramembrane protease is a rhomboid protease.

3. The method of claim 1, wherein the intramembrane protease is a γ-secretase.

4. The method of claim 1, wherein the intramembrane protease is a site-2 protease.

5. The method of claim 1, wherein the intramembrane protease is a presenilin homolog, prepilin peptidase, preflagellin peptidase or signal peptide peptidase.

6. The method of claim 1, wherein acidic conditions comprise about pH 3 to about pH 5.

7. The method of claim 1, wherein acidic conditions comprise about pH 4.

8. The method of claim 1, wherein acidic conditions comprise pH 4.

9. The method of claim 1, wherein physiological conditions comprise about pH 7.4.

10. The method of claim 1, wherein physiological conditions comprise pH 7.4.

11. The method of claim 1, wherein the substrate comprises a detectable label.

12. The method of claim 11, wherein the detectable label is conjugated to the amino terminus of the substrate.

13. The method of claim 11, wherein the detectable label is conjugated to the carboxy terminus of the substrate.

14. The method of claim 11, wherein the detectable label is conjugated to the extracellular or intracellular domain of the substrate.

15. The method of claim 11, wherein the detectable label is a modified side chain at any internal position of the substrate.

16. A method of screening for modulators of an intramembrane rhomboid protease comprising the steps of:
   a. contacting in a mixture the protease and a substrate with a lipid at pH 4.0 to (i) form a membrane comprising the lipid bilayer, protease and the substrate and (ii) render the protease catalytically inactive;
   b. contacting a test agent with the membrane mixture;
   c. raising the pH to pH 7.4 to render the protease catalytically active;
   d. assaying substrate cleavage by the protease; and
   e. comparing the assayed substrate cleavage to a reference that does not include the test agent, wherein an increase or a decrease of substrate cleavage by the protease relative to the reference identifies the test agent as a modulator of the intramembrane protease.

17. A method for identifying inhibitors of an intramembrane rhomboid protease comprising the steps of:
   a. contacting in a mixture the protease and a substrate with a lipid at pH 4.0 to (i) form a membrane comprising the lipid bilayer, protease and the substrate and (ii) render the protease catalytically inactive;
   b. contacting a test agent with the membrane mixture;
   c. raising the pH to pH 7.4 to render the protease catalytically active;
   d. assaying substrate cleavage by the protease; and
   e. comparing the assayed substrate cleavage to a reference that does not include the test agent, wherein a decrease of substrate cleavage by the protease relative to the reference identifies the test agent as an inhibitor of the intramembrane rhomboid protease.

18. A method for identifying agonists of an intramembrane rhomboid protease comprising the steps of:
   a. contacting the protease and a substrate with a lipid at pH 4.0 to (i) form a membrane comprising the lipid bilayer, protease and the substrate and (ii) render the protease catalytically inactive;
   b. contacting a test agent with the membrane mixture;
   c. raising the pH to pH 7.4 to render the protease catalytically active;
   d. assaying substrate cleavage by the protease; and
   e. comparing the assayed substrate cleavage to a reference that does not include the test agent, wherein an increase of substrate cleavage by the protease relative to the reference identifies the test agent as an agonist of the intramembrane rhomboid protease.

* * * * *

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: N-terminal FITC-TatA cleavage product.

<400> SEQUENCE: 1

Met Glu Ser Thr Ile Ala Thr Ala Ala Phe Gly Ser Pro
1               5                   10

<210> SEQ ID NO 2
```

```
<211> LENGTH: 15
<212> TYPE: PRT
<213> ORGANISM: Artificial Sequence
<220> FEATURE:
<223> OTHER INFORMATION: FITC-TatA WT

<400> SEQUENCE: 2

Met Glu Ser Thr Ile Ala Thr Ala Ala Phe Gly Ser Pro Trp Gln
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: FITC-TatA G11V+S12V

<400> SEQUENCE: 3

Met Glu Ser Thr Ile Ala Thr Ala Ala Phe Val Val Pro Trp Gln
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: GITC-TatA I5A F10A

<400> SEQUENCE: 4

Met Glu Ser Thr Ala Ala Thr Ala Ala Ala Gly Ser Pro Trp Gln
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: FITC-Spitz

<400> SEQUENCE: 5

Pro Arg Pro Met Leu Glu Lys Ala Ser Ile Ala Ser Gly Ala Met
1               5                   10                  15
```